US009486178B2

(12) United States Patent
Sakimoto et al.

(10) Patent No.: US 9,486,178 B2
(45) Date of Patent: Nov. 8, 2016

(54) RADIATION TOMOGRAPHIC IMAGE GENERATING APPARATUS, AND RADIATION TOMOGRAPHIC IMAGE GENERATING METHOD

(75) Inventors: Tomonori Sakimoto, Kyoto (JP); Kazuyoshi Nishino, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 109 days.

(21) Appl. No.: 14/424,909

(22) PCT Filed: Aug. 31, 2012

(86) PCT No.: PCT/JP2012/005545
§ 371 (c)(1),
(2), (4) Date: Jun. 24, 2015

(87) PCT Pub. No.: WO2014/033792
PCT Pub. Date: Mar. 6, 2014

(65) Prior Publication Data
US 2015/0305702 A1   Oct. 29, 2015

(51) Int. Cl.
*G06K 9/00* (2006.01)
*A61B 6/00* (2006.01)
(Continued)

(52) U.S. Cl.
CPC .............. *A61B 6/5258* (2013.01); *A61B 6/025* (2013.01); *A61B 6/03* (2013.01); *A61B 6/12* (2013.01); *G06T 11/008* (2013.01)

(58) Field of Classification Search
CPC ............ A61B 6/00; G06T 11/00; G06K 9/00
USPC ....... 382/128, 129, 130, 131, 132, 133, 134; 378/4, 8, 21–27, 901; 600/407, 410, 600/411, 425, 427
See application file for complete search history.

(56) References Cited

U.S. PATENT DOCUMENTS 6,125,193 A * 9/2000 Han ...................... G06T 11/008
382/131
2001/0028696 A1   10/2001 Yamada et al.
(Continued)

FOREIGN PATENT DOCUMENTS

JP   2001-286463 A   10/2001
JP   2005-021345 A   1/2005
(Continued)

OTHER PUBLICATIONS

Extended European Search Report EP Application No. 12883942.0 dated Jul. 30, 2015.
(Continued)

*Primary Examiner* — Abolfazl Tabatabai
(74) *Attorney, Agent, or Firm* — McDermott Will & Emery LLP

(57) ABSTRACT

This invention identifies a metal area of actual measurement projection data from the actual measurement projection data and an actual measurement reconstruction image obtained by image reconstruction of the actual measurement projection data, to acquire metal area identification data. In the actual measurement projection data, a resulting image has pixel values in the metal area such as of wire or screws, for example, not so different from pixel values of other areas, which makes it difficult to identify the metal area accurately. However, the metal area can be identified with increased accuracy. Based on the metal area identification data, data replacement of the metal area of the actual measurement projection data p1 is carried out with data obtained from pixels adjacent the metal area, thereby to acquire replacement projection data, which is put to image reconstruction to generate a replacement reconstruction image without the metal area. Since the metal area is identified with increased accuracy, the tissue adjacent the metal area of the tomographic image (replacement reconstruction image) can be restored with increased accuracy.

8 Claims, 13 Drawing Sheets

(51) Int. Cl.
*A61B 6/12* (2006.01)
*G06T 11/00* (2006.01)
*A61B 6/02* (2006.01)
*A61B 6/03* (2006.01)
*A61B 5/05* (2006.01)

(56) References Cited

U.S. PATENT DOCUMENTS

2006/0227928 A1 10/2006 Timmer
2008/0247624 A1 10/2008 Scholz

FOREIGN PATENT DOCUMENTS

JP 2007-530086 A 11/2007
JP 2009-201840 A 9/2009

OTHER PUBLICATIONS

English translation International Search Report PCT/JP2012/005545 dated Oct. 2, 2012.
Notification of Reasons for Refusal Japanese Patent Application No. 2014-532576 dated Dec. 8, 2015 with English translation.

* cited by examiner (a)

(b)

(c)

(d)

(a)

(b)

(a)

(b)

(a)

(b)

(c)

RADIATION TOMOGRAPHIC IMAGE GENERATING APPARATUS, AND RADIATION TOMOGRAPHIC IMAGE GENERATING METHOD

RELATED APPLICATIONS

This application is the U.S. National Phase application under 35 U.S.C. §371, of international Application No. PCT/JP2012/005545 filed on Aug. 31, 2012, the disclosure of which Application is incorporated by reference herein.

TECHNICAL FIELD

This invention relates to a radiation tomographic image generating apparatus and a radiation tomographic image generating method for generating radiation tomographic images by image reconstruction of projection data acquired from a plurality of different directions with respect to an inspection object.

BACKGROUND ART

As conventional radiation tomographic image generating apparatus, there are an X-ray tomographic apparatus which is capable of tomosynthesis, and an X-ray CT apparatus (see Patent Document 1, for example). Such a conventional apparatus has an X-ray tube for emitting X-rays toward an inspection object, an X-ray detector disposed opposite this X-ray tube for detecting X-rays transmitted through the inspection object, and an X-ray tomographic image generating device for generating X-ray (radiation) tomographic images (hereinafter called "tomographic images" as appropriate) from projection data (projection images) acquired by the X-ray detector.

The conventional apparatus, while moving the X-ray tube and the X-ray detector in an integrated or interlocked manner, acquires projection data by carrying out X-raying from a plurality of directions with respect to the inspection object. Tomographic images are acquired by operating the X-ray tomographic image generating device to carry out image reconstruction of the acquired projection data for a plurality of frames. Tomosynthesis is a technique for generating tomographic images of an arbitrary cutting height by collecting projection data for a plurality of frames through one tomographic operation, and by image reconstruction of the projection data for a plurality of frames.

Conventionally, when a high X-ray (radiation) absorber (hereinafter called "high absorber" as appropriate) in form of a metal, for example, is present in the inspection object, artifacts will appear in the tomographic images generated by carrying out image reconstruction since X-rays are shielded by the high absorber. So various methods for reducing the artifacts due to high absorbers have been proposed. In Patent Document 1, for example, a final tomographic image is acquired by the method of the flow chart shown in FIG. 14.

That is, actual measurement projection data is acquired first (step S101). A high absorber area is identified from the actual measurement projection data (step S102). Data replacement is carried out for the high absorber area of the actual measurement projection data with pixels adjacent the high absorber area (step S103). Image reconstruction is done from projection data resulting from the data replacement, to generate a first reconstruction image (step S104). Forward projection data is created by projecting the first reconstruction image forward (step S105). The forward projection data is adjusted, and the adjusted forward projection data is put to image reconstruction to generate a second reconstruction image (step S106). And a final tomographic image (reconstruction image) is acquired by carrying out the forward projection, adjustment and image reconstruction once or a plurality of times iteratively.

As described above, the conventional method obtains a tomographic image by erasing, through replacement, a high absorber area reflected in each of the actual measurement projection data, and reconstructing these. This acquires tomographic images which have reconstructed tissue around the high absorber with high accuracy, and have also reduced the artifacts around the high absorber. The conventional apparatus has a process for identifying the high absorber area reflected in the actual measurement projection data.

PRIOR ART DOCUMENT

Patent Document

[Patent Document 1]
Unexamined Patent Publication No. 2009-201840

SUMMARY OF INVENTION

Technical Problem

However, the conventional apparatus has a problem of being insufficient in identifying a high absorber area which causes artifacts in image reconstruction. That is, when identifying a high absorber area based only on actual measurement projection data, the conventional apparatus has difficulty in its identification. For example, thin objects such as wire and small objects such as screws will form images in which, although they may be high absorbers, their pixel values in the actual measurement projection data are not very different from those of areas other than the wire and the like.

It is therefore difficult to identify the high absorber area accurately, which makes it impossible to reconstruct tissue around the high absorber area in tomographic images with high accuracy. With the technique of Patent Document 1 noted above, although the high absorber ought to exist in the tomographic images, the result will be unnatural images as if the high absorber had disappeared from the tomographic images.

This invention has been made having regard to the state of the art noted above, and its first object is to provide a radiation tomographic image generating apparatus and a radiation tomographic image generating method capable of reconstructing tissue around a high absorber area in tomographic images with high accuracy.

A second object of this invention is to provide a radiation tomographic image generating apparatus and a radiation tomographic image generating method capable of obtaining tomographic images showing a high absorber in a high absorber area, while inhibiting artifacts due to the high absorber.

Solution to Problem

To fulfill the above object, this invention provides the following construction.

A radiation tomographic image generator of this invention comprises an actual measurement image reconstruction unit for carrying out image reconstruction of a plurality of actual measurement projection data acquired from different directions with respect to an inspection object including a high radiation absorber, to generate an actual measurement reconstruction image; a high absorber area identifying unit for identifying a high absorber area of the actual measurement projection data from the actual measurement projection data and the actual measurement reconstruction image, to acquire high absorber area identification data; a data replacing unit for carrying out, using the high absorber area identification data, data replacement of the high absorber area of the actual measurement projection data with data obtained from pixels adjacent the high absorber area, to acquire replacement projection data; a replacement image reconstruction unit for carrying out image reconstruction of the replacement projection data to generate a replacement reconstruction image; a difference processing unit for determining a difference between the actual measurement projection data and the replacement projection data to acquire difference projection data; a difference image reconstruction unit for carrying out image reconstruction of the difference projection data to generate a difference reconstruction image; and a composite image generating unit for generating a composite reconstruction image by selecting at least one image from among the actual measurement reconstruction image, the replacement reconstruction image and the difference reconstruction image on an area-by-area basis.

According to the radiation tomographic image generator of this invention, the actual measurement image reconstruction unit carries out image reconstruction of the actual measurement projection data to generate an actual measurement reconstruction image. The high absorber area identifying unit identifies a high absorber area of the actual measurement projection data from the actual measurement projection data and actual measurement reconstruction image to acquire high absorber area identification data. In the actual measurement projection data, for example, in a high absorber area such as of wire or screws, a resulting image has pixel values not so different from those of other areas, which makes it difficult to identify the high absorber area accurately. However, in the actual measurement reconstruction image, pixel values become remarkably large at boundaries between high absorber and body tissue, for example. By making use of this, boundaries between high absorber such as wire or screws and body tissue, for example, can be identified with increased accuracy. By using the actual measurement projection data in addition to the actual measurement reconstruction image, it is possible to discriminate whether the inside of the boundary between high absorber and body tissue is the high absorber, for example. With these, a high absorber area can be identified with increased accuracy. The data replacing unit, using the high absorber area identification data, carries out data replacement of the high absorber area of the actual measurement projection data with data obtained from pixels adjacent the high absorber area, thereby to acquire replacement projection data. The replacement image reconstruction unit generates the replacement reconstruction image without the high absorber area by image reconstruction of the replacement projection data. Since the high absorber area is identified with increased accuracy, the data replacement of the high absorber area can be carried out with increased accuracy. Therefore, the tissue adjacent the high absorber area of the tomographic image (replacement reconstruction image) can be restored with increased accuracy, while inhibiting artifacts due to the high absorber.

The difference processing unit determines a difference between the actual measurement projection data and the replacement projection data, to acquire difference projection data. The difference image reconstruction unit carries out image reconstruction of the difference projection data to generate a difference reconstruction image of only the high absorber area. And the composite image generating unit generates a composite reconstruction image by selecting at least one image from the actual measurement reconstruction image, replacement reconstruction image and difference reconstruction image on an area-by-area basis. That is, the composite reconstruction image is generated from not only the replacement reconstruction image but the actual measurement reconstruction image and difference reconstruction image. Since an optimal image is thereby selected for every area, a tomographic image (composite reconstruction image) showing a high absorber in the high absorber area can be obtained while inhibiting artifacts due to the high absorber.

In the radiation tomographic image generator of this invention, it is preferred that, of pixel values of the same coordinates in the actual measurement reconstruction image and the replacement reconstruction image, when the pixel value in the replacement reconstruction image is larger than the pixel value in the actual measurement reconstruction image, the composite image generating unit generates the composite reconstruction image by selecting the pixel value of the replacement reconstruction image. That is, in the actual measurement reconstruction image, pixels adjacent the high absorber area, because of the high absorber area, tend to have pixel values lower than their otherwise due pixel values. Therefore, by selecting pixel value of the replacement reconstruction image for the applicable pixels adjacent the high absorber area, the pixels adjacent the high absorber area can be approximated their due pixel values.

In the radiation tomographic image generator of this invention, it is preferred that, of pixel values of the same coordinates in the actual measurement reconstruction image, the replacement reconstruction image and the difference reconstruction image, when a sum of the pixel value in the replacement reconstruction image and the pixel value in the difference reconstruction image is smaller than the pixel value in the actual measurement reconstruction image, the composite image generating unit generates the composite reconstruction image by selecting a pixel value of the sum. That is, the pixel value of the high absorber area of the actual measurement reconstruction image tends to be over-evaluated at the time of image reconstruction to be a pixel value higher than its otherwise due pixel value. Therefore, by selecting the sum of the pixel value of the replacement reconstruction image and the pixel value of the difference reconstruction image for the applicable pixels of the high absorber area, the pixels of the high absorber area can be approximated their due pixel values.

In the radiation tomographic image generator of this invention, it is preferred that, of pixel values of the same coordinates in the actual measurement reconstruction image, the replacement reconstruction image and the difference reconstruction image, when a sum of the pixel value in the replacement reconstruction image and the pixel value in the difference reconstruction image is larger than the pixel value in the actual measurement reconstruction image, the composite image generating unit generates the composite reconstruction image by selecting the pixel value in the actual measurement reconstruction image. That is, the areas other than the area from which an appropriate pixel value is not acquired due to the high absorber, have selected therefor the pixel value of the actual measurement reconstruction image generated by image reconstruction of the actual measurement projection data as it is. Consequently, even if an area is discriminated by mistake as the high absorber area in the difference reconstruction image, for example, it is possible to preclude selection of the area discriminated by mistake.

In the radiation tomographic image generator of this invention, it is preferred that the high absorber area identifying unit, based on a graph cuts method, identifies the high absorber area of the actual measurement projection data from the actual measurement projection data and the actual measurement reconstruction image, to acquire the high absorber area identification data. This enables the high absorber area to be identified with high accuracy.

In the radiation tomographic image generator of this invention, it is preferred that the high absorber area identifying unit sets seed areas in the graph cuts method based on threshold process results of the actual measurement projection data and the actual measurement reconstruction image. Consequently, based on the threshold process result, the seed areas in the graph cuts method can be set automatically. This facilitates identification of the high absorber area.

In the radiation tomographic image generator of this invention, it is preferred that at least one of the actual measurement image reconstruction unit, the replacement image reconstruction unit and the difference image reconstruction unit carries out image reconstruction based on an iterative approximation method. Consequently, image reconstruction can be carried out with high accuracy.

A radiation tomographic image generating method of this invention comprises a step of carrying out image reconstruction of a plurality of actual measurement projection data acquired from different directions with respect to an inspection object including a high radiation absorber, to generate an actual measurement reconstruction image; a step of identifying a high absorber area of the actual measurement projection data from the actual measurement projection data and the actual measurement reconstruction image, to acquire high absorber area identification data; a step of carrying out, using the high absorber area identification data, data replacement of the high absorber area of the actual measurement projection data with data obtained from pixels adjacent the high absorber area, to acquire replacement projection data; and a step of carrying out image reconstruction of the replacement projection data to generate a replacement reconstruction image; and a step of generating a composite reconstruction image by selecting one image from the actual measurement reconstruction image and the replacement reconstruction image on an area-by-area basis.

According to the radiation tomographic image generating method of this invention, image reconstruction of the actual measurement projection data is carried out to generate an actual measurement reconstruction image. A high absorber area of the actual measurement projection data is identified from the actual measurement projection data and actual measurement reconstruction image to acquire high absorber area identification data. In the actual measurement projection data, for example, pixel values in a high absorber area such as of wire or screws will result in an image having pixel values not so different from those of other areas, which makes it difficult to identify the high absorber area accurately. However, in the actual measurement reconstruction image, pixel values become remarkably large at boundaries between high absorber and body tissue, for example. By making use of this, boundaries between high absorber such as wire or screw and body tissue, for example, can be identified with increased accuracy. By using the actual measurement projection data in addition to the actual measurement reconstruction image, it is possible to discriminate whether the inside of the boundary between high absorber and body tissue is the high absorber, for example. With these, a high absorber area can be identified with high accuracy. Using the high absorber area identification data, data replacement of the high absorber area of the actual measurement projection data is carried out with data obtained from pixels adjacent the high absorber area, thereby to acquire replacement projection data. The replacement reconstruction image without the high absorber area is generated by image reconstruction of the replacement projection data. Since the high absorber area is identified with increased accuracy, the data replacement of the high absorber area can be carried out with increased accuracy. Therefore, the tissue adjacent the high absorber area of the tomographic image (replacement reconstruction image) can be restored with increased accuracy, while inhibiting artifact due to the high absorber.

The composite image generating unit generates a composite reconstruction image by selecting one image from the actual measurement reconstruction image and the replacement reconstruction image an area-by-area basis. That is, the composite reconstruction image is generated from not only the replacement reconstruction image but the actual measurement reconstruction image. Since an optimal image is thereby selected for every area, a tomographic image (composite reconstruction image) showing a high absorber in the high absorber area can be obtained while inhibiting artifacts due to the high absorber.

Advantageous Effects of Invention

According to the radiation tomographic image generating apparatus and radiation tomographic image generating method of this invention, image reconstruction of the actual measurement projection data is carried out to generate an actual measurement reconstruction image. A high absorber area of the actual measurement projection data is identified from the actual measurement projection data and actual measurement reconstruction image to acquire high absorber area identification data. In the actual measurement projection data, for example, pixel values in a high absorber area such as of wire or screws will result in an image having pixel values not so different from those of other areas, which makes it difficult to identify the high absorber area accurately. However, in the actual measurement reconstruction image, pixel values become remarkably large at boundaries between high absorber and body tissue, for example. By making use of this, boundaries between high absorber such as wire or screw and body tissue, for example, can be identified with increased accuracy. By using the actual measurement projection data in addition to the actual measurement reconstruction image, it is possible to discriminate whether the inside of the boundary between high absorber and body tissue is the high absorber, for example. With these, a high absorber area can be identified with high accuracy. Using the high absorber area identification data, data replacement of the high absorber area of the actual measurement projection data is carried out with data obtained from pixels adjacent the high absorber area, thereby to acquire replacement projection data. The replacement reconstruction image without the high absorber area is generated by image reconstruction of the replacement projection data. Since the high absorber area is identified with increased accuracy, the data replacement of the high absorber area can be carried out with increased accuracy. Therefore, the tissue adjacent the high absorber area of the tomographic image (replacement reconstruction image) can be restored with increased accuracy, while inhibiting artifact due to the high absorber.

Further, according to this invention, a difference between the actual measurement projection data and the replacement projection data is determined to acquire difference projection data. The difference projection data is put to image reconstruction to generate a difference reconstruction image of only the high absorber area. And a composite reconstruction image is generated by selecting at least one image from the actual measurement reconstruction image, replacement reconstruction image and difference reconstruction image on an area-by-area basis. That is, the composite reconstruction image is generated from not only the replacement reconstruction image but the actual measurement reconstruction image and difference reconstruction image. Since an optimal image is thereby selected for every area, a tomographic image (composite reconstruction image) showing a high absorber in the high absorber area can be obtained while inhibiting artifact due to the high absorber.

DESCRIPTION OF EMBODIMENTS

Figure 1:
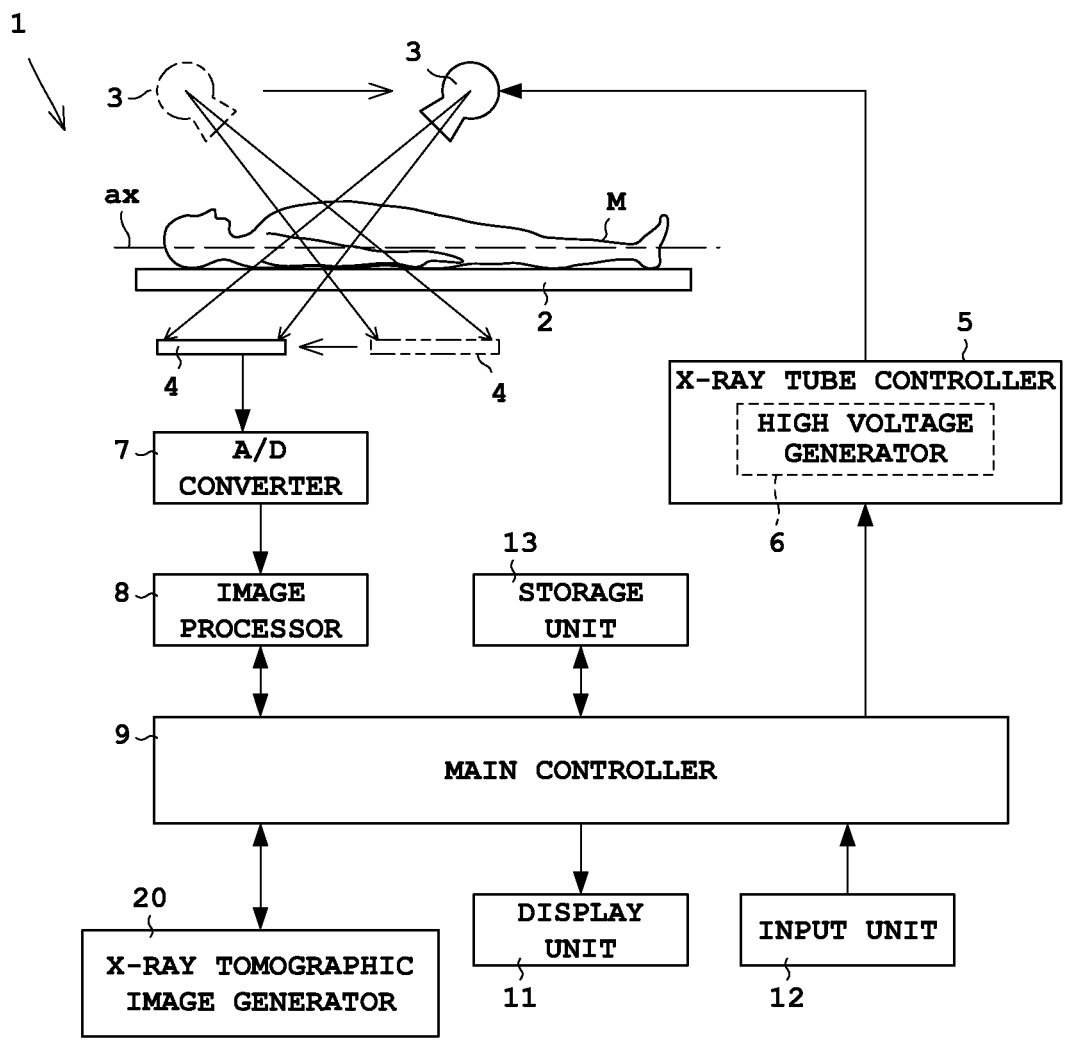
FIG. 1 is a view showing an outline construction of an X-ray tomographic apparatus according to an embodiment.

An embodiment of this invention will be described hereinafter with reference to the drawings. FIG. 1 is a view showing an outline construction of an X-ray tomographic apparatus according to the embodiment. The high absorber will be described taking metal as an example thereof.

Reference is made to FIG. 1. An X-ray tomographic apparatus 1 includes a top board 2 for supporting an inspection object M, an X-ray tube 3 for emitting X-rays toward the inspection object M, a flat panel X-ray detector (hereinafter called "FPD" as appropriate) 4 disposed opposite the X-ray tube 3 for detecting X-rays transmitted through the inspection object M. The FPD 4 corresponds to the actual measurement projection data acquiring unit in this invention.

The X-ray tube 3 is controlled by an X-ray tube controller 5. The X-ray tube controller 5 has a high voltage generator 6 for generating a tube voltage and a tube current for the X-ray tube 3. The X-ray tube controller 5 causes the X-ray tube 3 to emit X-rays according to X-ray emitting conditions such as tube voltage, tube current, and irradiation time.

The FPD 4 has numerous X-ray detecting elements arranged in rows and columns of a two-dimensional matrix array on an X-ray detecting plane to which transmitted X-ray images to be detected are projected. The detecting elements convert and detect the X-rays. The matrix array of X-ray detecting elements may, for example, be several thousands x several thousands. The X-ray detecting elements are the direct conversion type for converting X-rays directly into electric signals, or the indirect conversion type for converting X-rays once into light and then further converting it into electric signals.

The X-ray tube 3 and FPD 4 are synchronously movable parallel to each other in opposite directions along the body axis ax in FIG. 1 of the inspection object M. The X-ray tube 3 and FPD 4 are constructed drivable, for example, by racks, pinions and motors not shown. The FPD 4, while moving synchronously with and in the opposite direction to the X-ray tube 3, acquires actual measurement projection data for a plurality of frames (X-ray images) p1 from different directions (angles) with respect to the inspection object M including metal.

Downstream of the FPD 4 there are arranged in order an analog-to-digital converter 7, an image processor 8 and a main controller 9. The analog-to-digital converter 7 converts into digital signals the actual measurement projection data p1 outputted in analog form from the FPD 4, respectively. The image processor 8 carries out various required processes on the actual measurement projection data p1 having undergone the digital conversion. The main controller 9 performs overall control of the components of the X-ray tomographic apparatus 1, and is formed of a central processing unit (CPU) or the like. The main controller 9 carries out control to move the X-ray tube 3 or FPD 4, for example.

The X-ray tomographic apparatus 1 includes a display unit 11, an input unit 12 and a storage unit 13. The display unit 11 is in form of a monitor, for example. The input unit 12 includes a keyboard, a mouse and so on. The storage unit 13 may be storage media including removable media, such as a ROM (Read-only Memory), a RAM (Random-Access Memory) or a hard disk. The storage unit 13 stores the actual measurement projection data p1 for a plurality of frames, for example.

Figure 2:
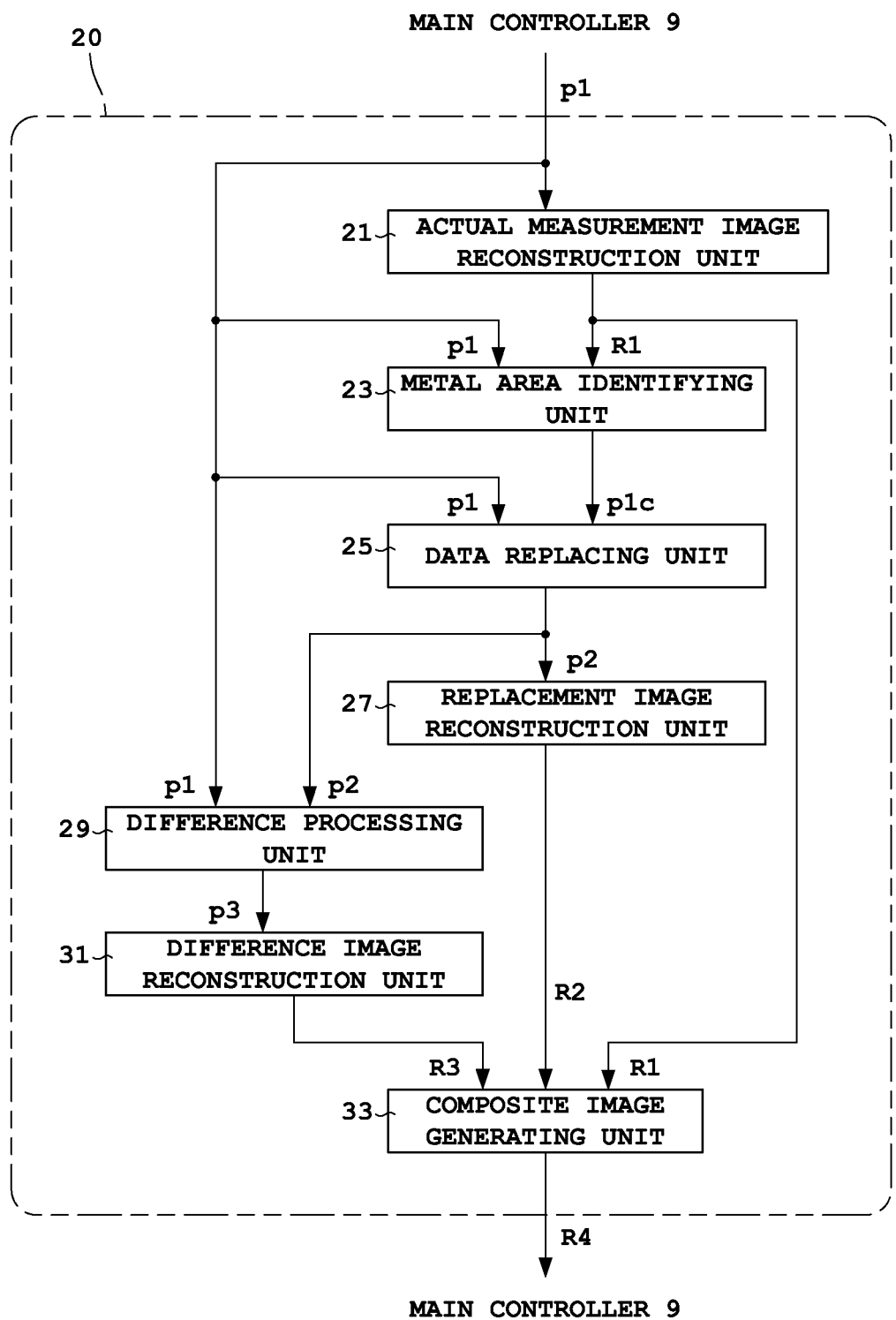
FIG. 2 is a view showing a construction of an X-ray tomographic image generator.

The X-ray tomographic apparatus 1 further includes an X-ray tomographic image generator 20 for generating tomographic images from the actual measurement projection data p1 for a plurality of frames acquired by the FPD 4. FIG. 2 is a view showing the construction of the X-ray tomographic image generator 20. The X-ray tomographic image generator 20 generates various tomographic images. The tomographic images generated by the X-ray tomographic image generator 20 include an actual measurement reconstruction image R1 in FIG. 3(a), a replacement reconstruction image R2 in FIG. 3(b), and a difference reconstruction image in FIG. 3(c). The X-ray tomographic image generator 20 further generates a composite reconstruction image R4 by selecting at least one image from among these tomographic images on a pixel-by-pixel basis. Note that the actual measurement reconstruction image R1 is a tomographic image of the actual measurement projection data p1 image-reconstructed as it is. The replacement reconstruction image R2 is a tomographic image without a metal area Y1. The difference reconstruction image R3 is a tomographic image of only the metal area Y1.

Figure 3:
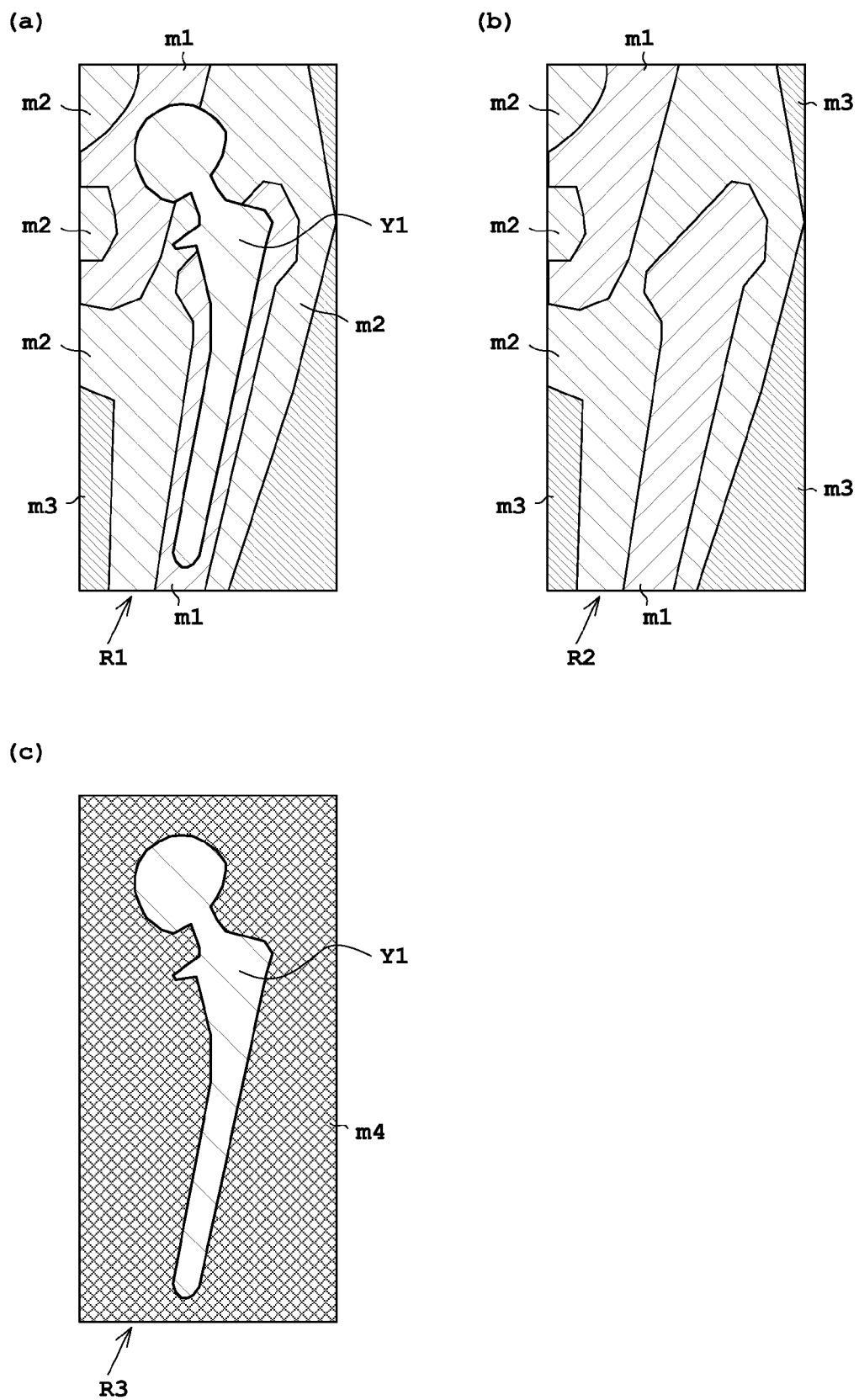
FIG. 3, (a) is a view showing an actual measurement reconstruction image, (b) is a view showing a replacement reconstruction image, and (c) is a view showing a difference reconstruction image.

In FIGS. 3(a)-3(c), sign m1 indicates bone tissue, and sign m2 indicates soft tissue such of muscle and skin. Sign m3 indicates areas other than the inspection object M, and sign m4 indicates areas other than the metal area Y1.

Reference is made to FIG. 2 again. The X-ray tomographic image generator 20 includes an actual measurement image reconstruction unit 21 for generating the actual measurement reconstruction image R1 by image reconstruction of the actual measurement projection data p1, and a metal area identifying unit 23 for identifying the metal area Y1 of the actual measurement projection data p1 from the actual measurement projection data p1 and actual measurement reconstruction image R1, thereby to acquire metal area identification data p1c. The X-ray tomographic image generator 20 also includes a data replacing unit 25 for carrying out, based on the metal area identification data p1c, data replacement of the metal area Y1 of the actual measurement projection data p1 with data Z obtained from pixels K adjacent the metal area Y1, thereby to acquire replacement projection data p2, and a replacement image reconstruction unit 27 for generating the replacement reconstruction image R2 by image reconstruction of the replacement projection data p2.

The X-ray tomographic image generator 20 includes a difference processing unit 29 for determining a difference between the actual measurement projection data p1 and the replacement projection data p2, thereby to acquire difference projection data p3 showing only pixel values of the metal area Y1, and a difference image reconstruction unit 31 for generating the difference reconstruction image R3 by image reconstruction of the difference projection data p3. Further, the X-ray tomographic image generator 20 includes a composite image generating unit 33 for generating the composite reconstruction image R4 by selecting at least one image from among the actual measurement reconstruction image R1, replacement reconstruction image R2 and difference reconstruction image R3 on a pixel-by-pixel basis. Next, each component of the X-ray tomographic image generator 20 will particularly be described.

The metal area identification data corresponds to the high absorber area identification data in this invention. The metal area identifying unit 23 corresponds to the high absorber area identifying unit in this invention. The X-ray tomographic image generator 20 corresponds to the radiation tomographic image generating apparatus of this invention.

<Actual Measurement Image Reconstruction Unit>

The actual measurement image reconstruction unit 21 carries out image reconstruction of the actual measurement projection data p1 for a plurality of frames acquired from different directions with respect to the inspection object M including metal, to generate the actual measurement reconstruction image R1 which is a kind of tomographic image. That is, the actual measurement image reconstruction unit 21 carries out image reconstruction of the actual measurement projection data p1 as it is, to generate the actual measurement reconstruction image RE For image reconstruction, one of an iterative approximation method and an FBP (filtered back-projection) method is used, for example. As the iterative approximation method, for example, ML-EM (maximum likelihood-expectation maximization) method, OS-EM (ordered subsets-expectation maximization) method, RAMLA (row-action maximum likelihood algorithm) method or DRAMA (dynamic RAMLA) method is used.

<Metal Area Identifying Unit>

The metal area identifying unit 23, based on a graph cuts method, acquires metal area identification data (projection data) p1c which identifies the metal area Y1 of the actual measurement projection data p1 from the actual measurement projection data p1 and actual measurement reconstruction image R1.

Figure 4:
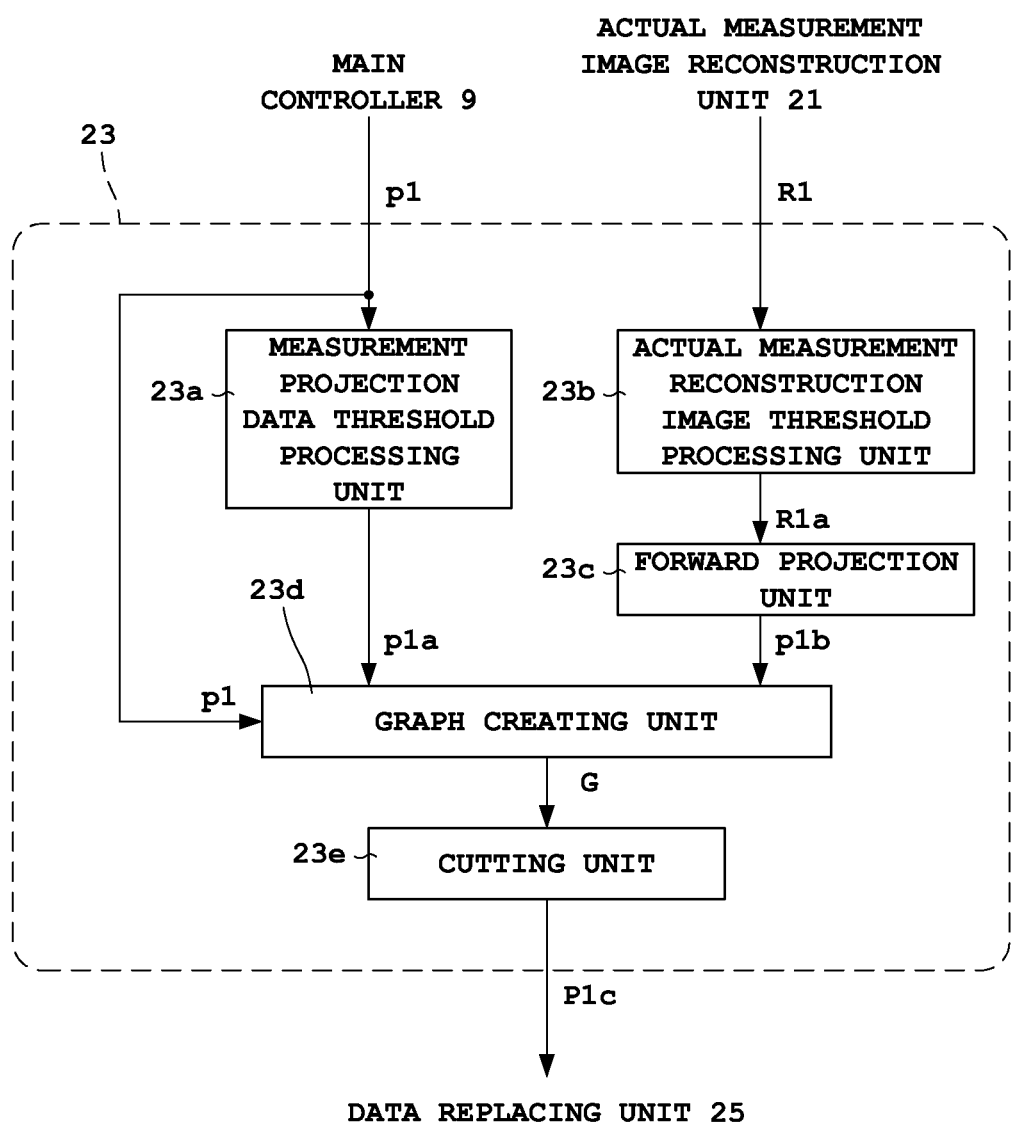
FIG. 4 is a view showing a construction of a metal area identifying unit.

FIG. 4 is a view showing the construction of the metal area identifying unit 23. An outline of each component of the metal area identifying unit 23 will be described. The metal area identifying unit 23 includes an actual measurement projection data threshold processing unit 23a for carrying out a threshold process of the actual measurement projection data p1 to acquire projection data p1a (see FIG. 5(a)) after the threshold process. Further, the metal area identifying unit 23 includes an actual measurement reconstruction image threshold processing unit 23b for carrying out a threshold process of the actual measurement reconstruction image R1 to acquire a binarized actual measurement reconstruction image R1a, and a forward projection unit 23c for carrying out forward projection of the binarized actual measurement reconstruction image R1a to acquire forward projection data p1b (see FIG. 5(b)).

Figure 5:
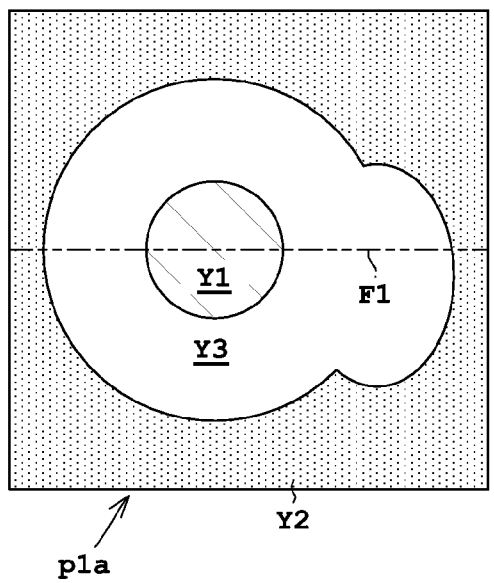
FIG. 5, (a) is a view showing actual measurement projection data after a threshold process; (b) is a view showing forward projection data, (c) is a view showing a seed region of a graph, and (d) is a view showing metal area identification data.
Figure 5:
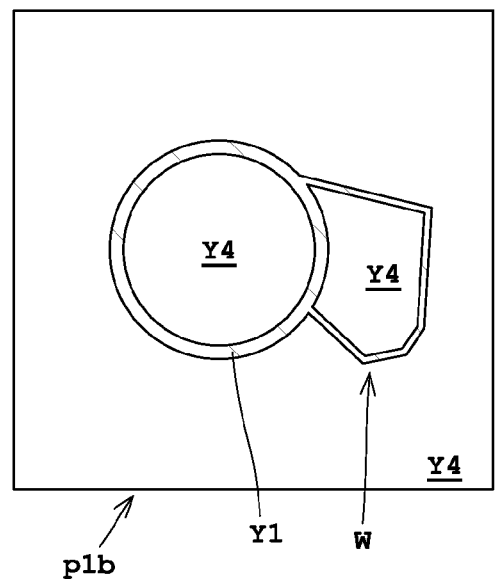
Figure 5:
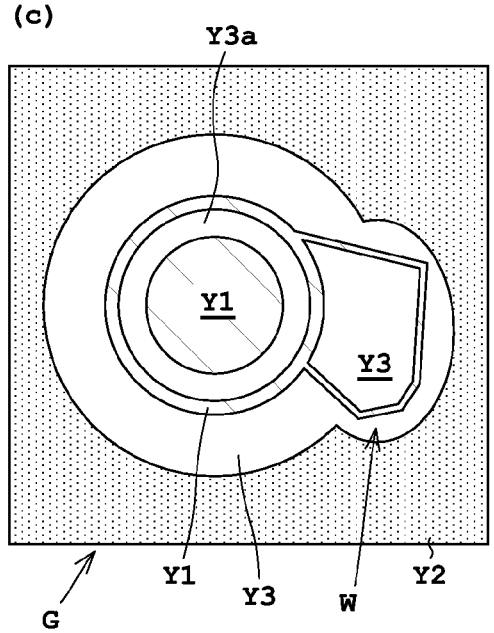
Figure 5:
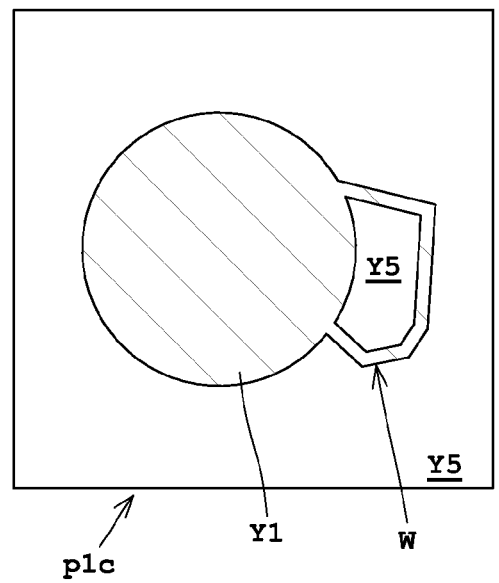

And the metal area identifying unit 23 includes a graph creating unit 23d for creating a graph G (see FIG. 5(c)) for identifying metal area Y1, using the projection data p1a after the threshold process and the forward projection data p1b, and a cutting unit 23e for acquiring metal area identification data p1c (see FIG. 5(d)) which is projection data identifying the metal area Y1 by cutting the graph G. Details of the graph cuts method will be described hereinafter. In FIGS. 5(b)-5(d), sign W indicates a wire portion. For expediency of explanation, the projection data p1a after the threshold process and others shown in FIGS. 5(a)-5(d) are represented by circular metal area Y1 and wire W (which applies also to FIGS. 13(a)-13(c) described hereinafter). Therefore, the replacement reconstruction image R2 of FIG. 3(b), for example, is not acquired directly from metal area identification data p1c of FIG. 5(d). Areas Y4 are areas without data, and areas Y5 are nonmetal areas.

Figure 6:
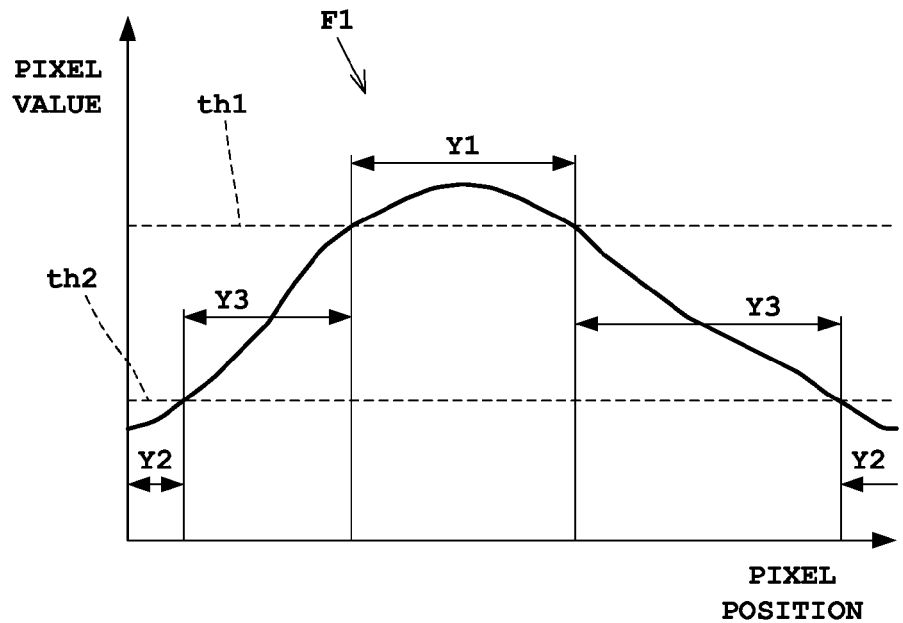
FIG. 6 is a profile illustrative of the threshold process on the actual measurement projection data.
Figure 7:
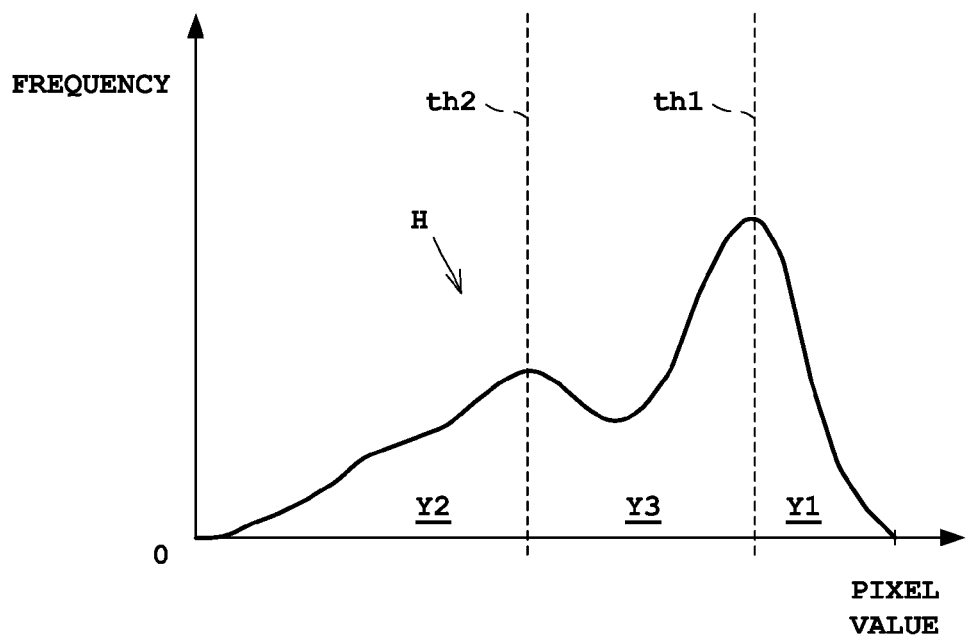
FIG. 7 is a histogram illustrative of the threshold process on the actual measurement projection data.

Next, each component of the metal area identifying unit 23 will be described more specifically. The actual measurement projection data threshold processing unit 23a acquires the actual measurement projection data p1a after the threshold process by carrying out a threshold process of the actual measurement projection data p1. FIG. 6 is a view showing an example of profile of the actual measurement projection data p1. As shown in FIG. 6, the metal area Y1 which is positively metal is first distinguished by a threshold process (threshold th1). A nonmetal area Y2 which is positively nonmetal is distinguished by a threshold process (threshold th2). Consequently, the actual measurement projection data p1 is divided into three areas, i.e. into the positively metal area Y1, the positively nonmetal area Y2 and an obscure area Y3 which is undistinguishable. It is assumed that FIG. 6 is located in the position of sign F1 in FIG. 5(a). FIG. 7 is a view showing an example of histogram H which shows frequencies for pixel values of all the pixels of the actual measurement projection data p1. The thresholds th1 and th2 are set beforehand from the histogram H.

On the other hand, the actual measurement reconstruction image threshold processing unit 23b carries out a threshold process on the actual measurement reconstruction image R1 having become a tomographic image, to divide it into the metal area Y1 and the areas other than metal. That is, the actual measurement reconstruction image threshold processing unit 23b acquires the binarized actual measurement reconstruction image R1a through the threshold process (binarization process) by setting the metal area Y1 to "1" and setting the areas other than metal to "0". The actual measurement reconstruction image threshold processing unit 23b generates the binarized actual measurement reconstruction image R1a for each actual measurement reconstruction image R1.

Figure 8:
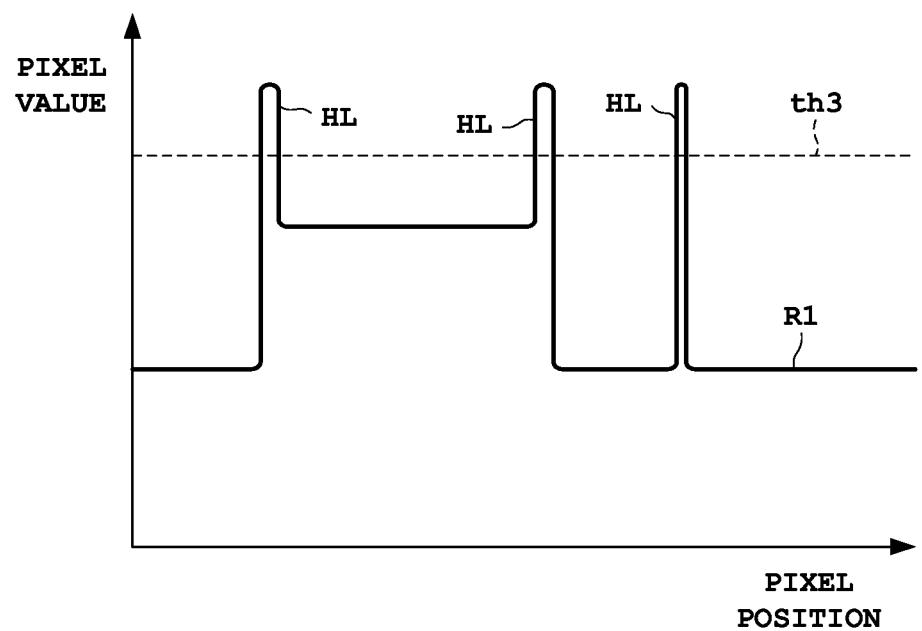
FIG. 8, (a) is a profile illustrative of the threshold process on the actual measurement reconstruction image, and (b) is a view showing an actual measurement reconstruction image after the threshold process.
Figure 8:
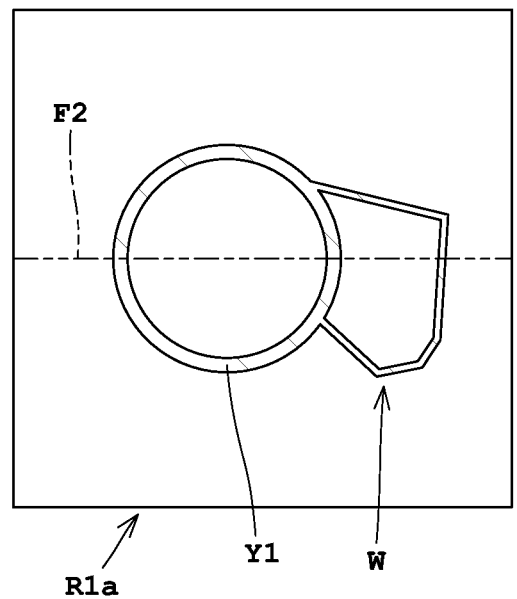

FIG. 8(a) is a view showing an example of profile of the actual measurement reconstruction image R1. Reconstruction images (e.g. the actual measurement reconstruction image R1) generated by many reconstruction algorithms such as by iterative approximation, for example, have remarkably large pixel values in portions with high luminance difference (high pixel value difference) edges (hereinafter called "high luminance edge portions") HL. The high luminance edge portions may be boundaries between metal and body tissue (bone or soft tissue), for example. The actual measurement reconstruction image threshold processing unit 23b extracts the high luminance edge portions HL by the threshold process (threshold th3) as shown in FIG. 8(a).

FIG. 8(b) is a view showing an example of the binarized actual measurement reconstruction image R1a. Sign F2 indicates data parts after the threshold process of FIG. 8(a). When the metal area Y1 in the actual measurement reconstruction image R1 has a circle shape, the high luminance edge portions HL are extracted in the shape of a doughnut in the binarized actual measurement reconstruction image R1a. When this binarized actual measurement reconstruction image R1a is projected forward, the high luminance edge portions HL will appear in the shape of a doughnut on the forward projection data p1b. The high luminance edge portions HL in the shape of a doughnut, when the method of acquiring actual measurement projection data and the like is tomosynthesis as in this embodiment, for example, will appear when there is no actual measurement projection data from certain directions.

The forward projection unit 23c projects forward the binarized actual measurement reconstruction image R1a. The forward projection data p1b is acquired, in which the metal area Y1 is an area where the pixel values acquired from the forward projection are not zero "0", and the areas Y4 without data are areas where the pixel value is zero (see FIG. 5(b)).

The graph creating unit 23d creates the graph G for use in the graph cuts method. This graph cuts method is a method which generates the graph G based on the actual measurement projection data p1, the projection data p1a after the threshold process, and the forward projection data p1b, and divides areas of the graph G based on these. The graph cuts method therefore first creates the graph G shown in FIG. 9 from these three images. The graph G includes nodes N corresponding to the respective pixels of the actual measurement projection data p1, two terminals S and T, and edges (sides) extending between the nodes and between node terminals. The nodes correspond to the respective pixels of the actual measurement projection data p1, and the two terminals S and T are expressed by metal and non-metal. The graph G is created by setting a cost given to each edge based on the actual measurement projection data p1. However, for the nodes corresponding to the pixels that have been regarded in the process up to this point as positively representing metal, that is the nodes which will become metal-side seeds, the edges extending between these nodes and the metal-side terminal are given costs which are positively not to be cut, and the edges extending between these nodes and the nonmetal-side terminal are given cost 0. Similarly, for the nodes corresponding to the pixels that have been regarded in the process up to this point as positively representing nonmetal, that is the nodes which will become nonmetal-side seeds, the edges extending between these nodes and the nonmetal-side terminal are given costs which are positively not to be cut, and the edges extending between these nodes and the metal-side terminal are given cost 0. Subsequently, the graph G is divided into areas according to the costs given to the edges, thereby dividing the image interior into metal and nonmetal. This completes the area division by the graph cuts method.

Figure 9:
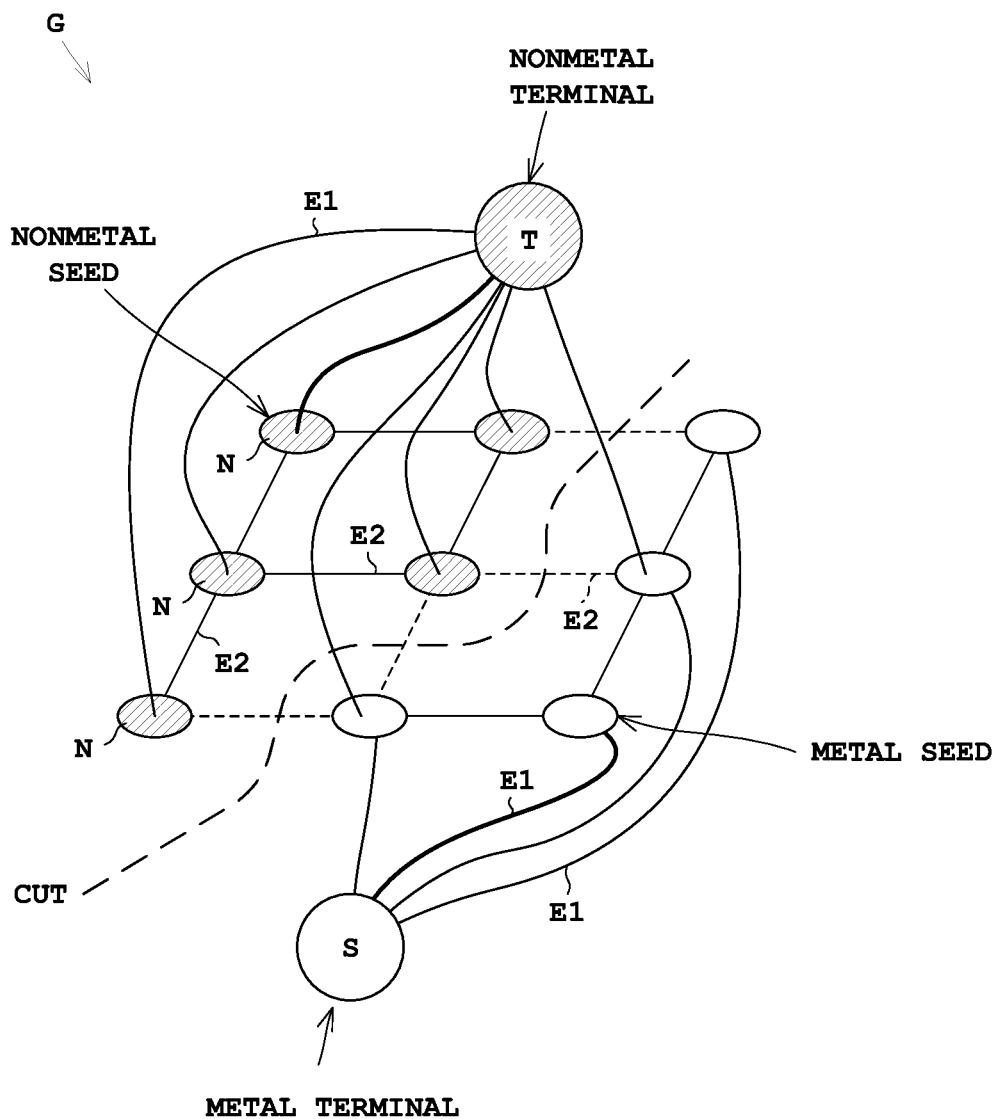
FIG. 9 is a view illustrative of a graph cuts method.

A method of generating the graph G will be described specifically. The graph G created at this time, as shown in FIG. 9, includes nodes N corresponding to the respective pixels of the actual measurement projection data p1, metal terminal S and nonmetal terminal T. The graph creating unit 23d sets costs of the edges in the graph cuts method based on threshold process results of the actual measurement projection data p1 and actual measurement reconstruction image R1, the pixel value of the nodes, and pixel value differences between adjoining nodes. However, seed areas are set from the projection data p1a after the threshold process, and the forward projection data p1b, and the above costs are set to the edges extending between nodes and terminals corresponding to the seed areas. The nodes forming the seed areas are determined by the following method. The graph creating unit 23d, for each node N in the graph G, sets as metal and nonmetal seeds the areas discriminated to be the metal area Y1 or nonmetal area Y2 in the projection data p1a after the threshold process (see FIG. 5(c)). Similarly, the graph creating unit 23d, for each node N in the graph G, sets as seed of the high absorber the area discriminated to be the metal area Y1 in the forward projection data p1b (see FIG. 5(c)).

Edge E1 is given cost C1 based on the respective pixel values of the actual measurement projection data p1. Edges E2 extending between the nodes are given cost C2 based on the pixel value differences between the respective pixels of the actual measurement projection data p1. Cost C2 given to the edges E2 has the smaller value, the larger the pixel value difference is between the respective pixels. Costs C1 and C2 serve as indexes for the area division.

In the obscure area Y3 (see FIG. 5(c)) of the graph G created by setting the seeds and costs C1 and C2, the cutting unit 23e divides the obscure area Y3 of each graph G so that a sum total of costs C2 of cut portions become a minimum. This identifies the metal area Y1. The cutting unit 23e outputs the metal area identification data (projection data) p1c which extracts only the metal area Y1. In the graph G with the seeds set as shown in FIG. 5(c), cost C2 of the obscure area Y3a becomes large since the pixel value difference between each pixel of the obscure area Y3a and the surroundings in the actual measurement projection data p1 is small. Therefore, the obscure area Y3a will remain uncut.

<Data Replacing Unit>

Figure 10:
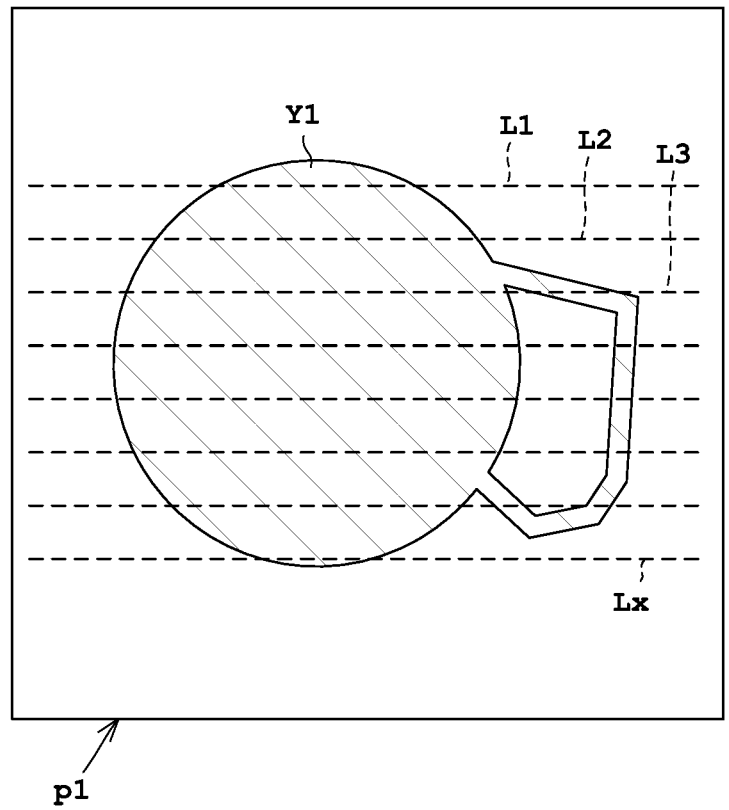
FIG. 10, (a) is a view showing the actual measurement projection data illustrative of a data replacing unit, and (b) is a profile of crossing line L1 of (a)
Figure 10:
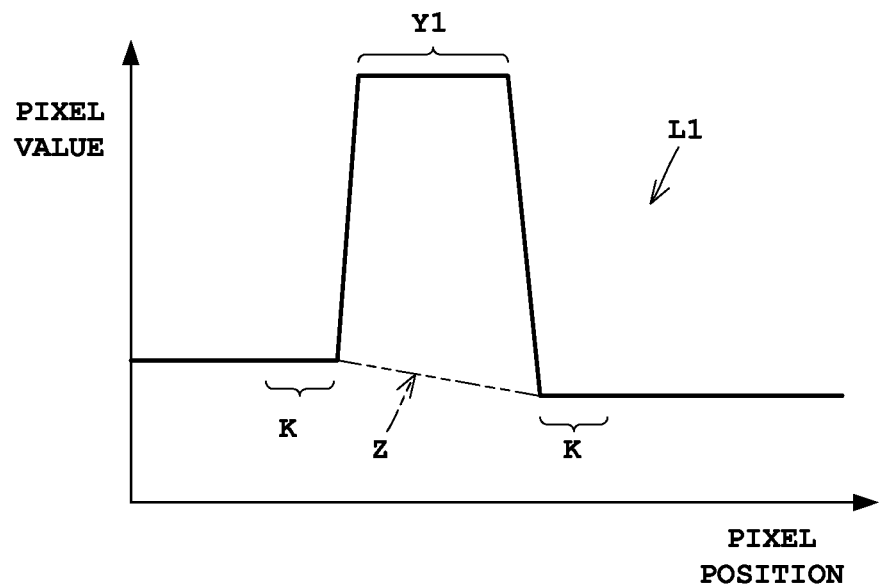

Reference is made to FIG. 2 again. The data replacing unit 25 carries out data replacement of the identified metal area Y1 of the actual measurement projection data p1 with data Z obtained from pixels K adjacent the metal area Y1, thereby to acquire replacement projection data p2. The data replacement is carried out such that, when there are cross lines (L1, L2, . . . , Lx) crossing the metal area Y1 as shown in FIG. 10(a), for example, pixel values are replaced in a way to connect two pixels outside the metal area Y1. FIG. 10(b) shows replacement data Z. The replacement data Z linearly connects the two pixel values for replacing the pixel values, but the connection may form a curve line. The data replacement may be followed by a further, smoothing process for adapting the pixel values. This process uses a two-dimensional Gaussian filter or median filter, for example. Note that the data replacement may be carried out by other known methods.

<Replacement Image Reconstruction Unit>

The replacement image reconstruction unit 27 generates the replacement reconstruction image R2 by image reconstruction of the replacement projection data p2. The generated replacement reconstruction image R2 is an image without the metal area Y1. The image reconstruction, similarly, uses one of the iterative approximation method and the FBP method, for example.

<Difference Processing Unit and Difference Image Reconstruction Unit>

The difference processing unit 29 determines a difference between the actual measurement projection data p1 and the replacement projection data p2, to acquire difference projection data p3 showing only the metal area Y1. The difference image reconstruction unit 31 generates the difference reconstruction image R3 by image reconstruction of the difference projection data p3. The generated difference reconstruction image R3 is an image of only the metal area Y1. The image reconstruction uses the iterative approximation method, for example.

<Composite Image Generating Unit>

The actual measurement reconstruction image R1, replacement reconstruction image R2 and difference reconstruction image R3 are sent to the composite image generating unit 33, and are stored in a storage unit not shown. The composite image generating unit 33 generates the composite reconstruction image R4 by selecting at least one image from among the actual measurement reconstruction image R1, replacement reconstruction image R2 and difference reconstruction image R3 on a pixel-by-pixel basis. Here, the actual measurement reconstruction image R1 is a tomographic image generated based on the actual measurement projection data p1, which includes the metal area Y1. The replacement reconstruction image R2 is a tomographic image obtained by reconstruction of an image group (replacement projection data p2) produced from the actual measurement projection data p1 with the metal area Y1 erased therefrom. The difference reconstruction image R3 is a tomographic image obtained by reconstruction of an image group (difference projection data p3) which is a difference between the actual measurement projection data p1 and replacement projection data p2.

The actual measurement reconstruction image R1 has dark false images occurring around the metal area Y1, which should not be allowed to appear on the composite reconstruction image R4. The metal area Y1 included in the actual measurement reconstruction image R1 shows irregularities, which also should not be allowed to appear on the composite reconstruction image R4. The metal area Y1 is erased from the replacement reconstruction image R2, which alone does not constitute an image well suited for diagnosis. Similarly, the difference reconstruction image R3 is an image showing only the metal area Y1 this time, which alone does not constitute an image well suited for diagnosis. So the composite image generating unit 33, by combining these three tomographic images, generates the composite reconstruction image R4 which is a tomographic image well suited for diagnosis. The composite image generating unit 33 will be described with reference to the flow chart of FIG. 11.

[Step S01] Extract Pixel Values

Arbitrary pixel values r1, r2 and r3 of the same coordinates in the actual measurement reconstruction image R1, replacement reconstruction image R2 and difference reconstruction image R3 are extracted.

[Step S02] First Pixel Value Comparison

The composite image generating unit 33, when pixel value r2 of the replacement reconstruction image R2 is larger than pixel value r1 of the actual measurement reconstruction image R1 (r2>r1), selects pixel value r2 of the replacement reconstruction image R2, and sets it as pixel value r4 of the composite reconstruction image R4. That is, when the pixel values are r2>r1, the composite image generating unit 33 selects pixel value r2, and proceeds to step S04. In this step, the pixels forming the dark false images on the actual measurement reconstruction image R1 are not used for the composite reconstruction image R4, but instead the pixels in the same positions on the replacement reconstruction image R2 are used. Consequently, the dark false images on the actual measurement reconstruction image R1 do not appear on the composite reconstruction image R4.

The replacement reconstruction image R2 is an image without the metal area Y1. In the actual measurement reconstruction image R1, pixels adjacent the metal area Y1, because of the metal area Y1, tend to have pixel values lower than their otherwise due pixel values. Therefore, by selecting pixel value r2 of the replacement reconstruction image R2 for the applicable pixels adjacent the metal area, the pixels adjacent the metal area can be approximated their due pixel values (correction of the undershooting pixel values).

The composite image generating unit 33, when in step S02 pixel value r2 of the replacement reconstruction image R2 is smaller than pixel value r1 of the actual measurement reconstruction image R1 (r2<r1), proceeds to step S03. When the pixel values are r2=r1, whichever of the pixel values r1 and r2 may be selected. In order to simplify the process, pixel value r2 may be selected when, for example, the pixel values are r2>r1, and the operation may proceed to step S04.

[Step S03] Second Pixel Value Comparison

When the sum (r2+r3) of pixel value r2 of the replacement reconstruction image R2 and pixel value r3 of the difference reconstruction image R3 is smaller than pixel value r1 of the actual measurement reconstruction image R1 (r2+r3<r1), the composite image generating unit 33 selects the pixel value of the sum (r2+r3) and sets it as pixel value r4 of the composite reconstruction image R4. That is, when the pixel values are r2+r3<r1, the composite image generating unit 33 selects the pixel value (r2+r3), and proceeds to step S04. In this step, bright areas (over-evaluated areas) of the metal area on the actual measurement reconstruction image R1 are not used for the composite reconstruction image R4, but instead the pixels of the sum (r2+r3) are used. This prevents the bright areas of the metal area on the actual measurement reconstruction image R1 from appearing on the composite reconstruction image R4. Consequently, the metal area on the composite reconstruction image R4 shows no irregularity.

Pixel value r1 of the metal area Y1 of the actual measurement reconstruction image R1 tends to be over-evaluated at the time of image reconstruction to be a pixel value higher than its otherwise due pixel value. Therefore, by selecting the sum (r2+r3) of pixel value r2 of the replacement reconstruction image R2 and pixel value r3 of the difference reconstruction image R3 for the applicable pixels of the metal area Y1, the pixels of the high absorber area can be approximated their due pixel values (correction of the overshooting pixel values such as of the metal area Y1).

When in step S03 the sum (r2+r3) of pixel value r2 of the replacement reconstruction image R2 and pixel value r3 of the difference reconstruction image R3 is larger than pixel value r1 of the actual measurement reconstruction image R1 (r2+r3 >r1), the composite image generating unit 33 selects pixel value r1 of the actual measurement reconstruction image R1, and sets it as pixel value r4 of the composite reconstruction image R4. That is, when both step SO2 and step S03 select "not applicable (NO)", the composite image generating unit 33 selects pixel value r1 of the image R1, and proceeds to step SO4.

The areas other than the area for which "YES" is selected in either one of step S02 and step S03, and from which an appropriate pixel value is not acquired due to the metal, have selected therefor pixel value r1 of the actual measurement reconstruction image R1 generated by image reconstruction of the actual measurement projection data p1 as it is. Consequently, even if an area is discriminated by mistake as the metal area Y1 in the difference reconstruction image R3, for example, it is possible to preclude selection of the area discriminated by mistake.

When the pixel values are r2+r3=r1, whichever of the pixel values (r2+r3) and r1 may be selected. In order to simplify the process, when the pixel values are r2+r3≤r1, pixel value (r2+r3) may be selected, and the operation may proceed to step S04.

[Step S04] Generation of Composite Reconstruction Image

The composite image generating unit 33 gives the pixel values (r2, r2+r3, r1) of images R1-R3 selected in step S02 and step S03 to the pixels r4 of the corresponding coordinates in the composite reconstruction image R4. The composite reconstruction image R4 is generated based on this.

[Step S05] Is Composite Reconstruction Image Completed?

When the composite reconstruction image R4 is incomplete, for example, a next pixel r4 is designated and the operation returns to step S01 in order to generate pixel r4 in an incomplete portion of the composite reconstruction image R4. When the composite reconstruction image R4 is completed (when the selection of all pixels r4 of the composite reconstruction image R4 is completed), the process is ended (END). The composite image generating unit 33 generates the composite reconstruction image R4 as described above.

Figure 12:
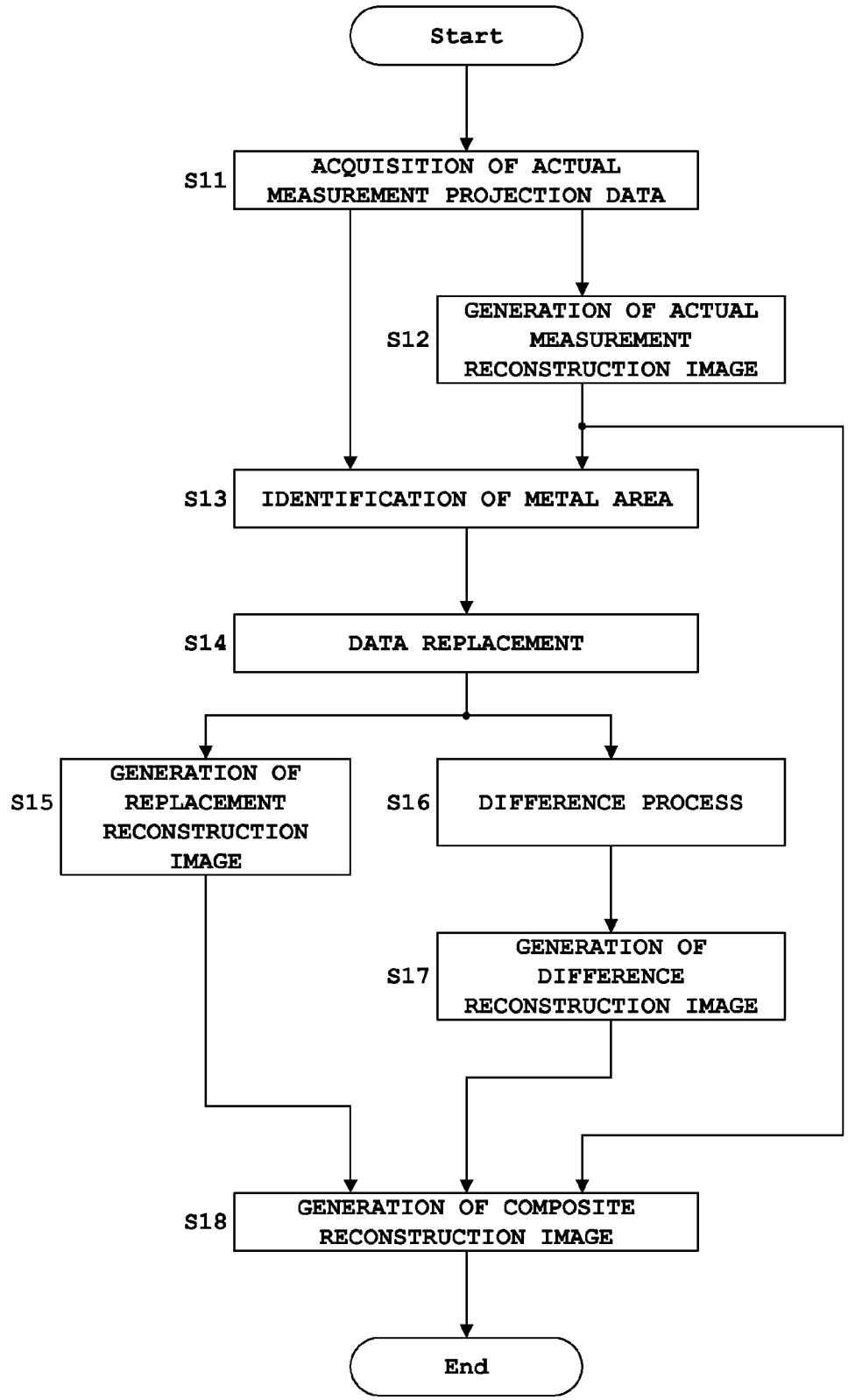
FIG. 12 is a flow chart showing operation of the X-ray tomographic apparatus according to the embodiment.

Next, operation of the X-ray tomographic apparatus 1 will be described with reference to FIG. 12.

[Step S11] Acquisition of Actual Measurement Projection Data

The X-ray tube 3 and FPD 4, while moving in parallel, synchronously with and in opposite directions to each other along the body axis ax in FIG. 1 of the inspection object M. At this time, the X-ray tube 3 emits X-rays toward the inspection object M, and the FPD 4 detects X-rays transmitted through the inspection object M. The FPD 4 acquires the actual measurement projection data p1 from a plurality of different directions with respect to the inspection object M including metal. The actual measurement projection data p1 is stored in the storage unit 13.

[Step S12] Generation of Actual Measurement Reconstruction Image

The actual measurement image reconstruction unit 21 carries out image reconstruction of the actual measurement projection data p1 to generate the actual measurement reconstruction image R1 (see FIG. 3(a)).

[Step S13] Identification of Metal Area

The metal area identifying unit 23, based on the graph cuts method, identifies the metal area Y1 of the actual measurement projection data p1 from the actual measurement projection data p1 and actual measurement reconstruction image R1 to acquire metal area identification data p1c. First, the metal area identifying unit 23 determines seed areas in the graph cuts method based on threshold process results of the actual measurement projection data p1 and actual measurement reconstruction image R1.

The threshold process carried out on the actual measurement projection data p1 obtains the metal area Y1 reliably and the nonmetal area Y2 reliably. This provides three divided areas consisting of the metal area Y1, nonmetal area Y2 and undistinguishable area Y3. The metal area Y1 and nonmetal area Y2 are set as seeds of the graph G in the graph cuts method. On the other hand, the threshold process (binarization process) carried out on the actual measurement reconstruction image R1 acquires the binarized actual measurement reconstruction image R1a having two divided areas, i.e. the metal area set to "1" and the nonmetal area set to "0". The binarized actual measurement reconstruction image R1a is projected forward, to acquire the forward projection data p1b in which the area with pixel values obtained from the forward projection not being zero "0" is the metal area, and the area with pixel values being zero is the area having no data. The metal area Y1 of the acquired forward projection data p1b is set as seed.

Cost C2 between the respective pixels of the actual measurement projection data p1 is given the smaller value, the larger the pixel value difference is between the respective pixels, for example. The graph G is created by setting the seeds, and costs C1 and C2. In the obscure area Y3 not set as seed in the graph G, the obscure area Y3 of each graph G is divided so that a sum total of costs C2 become a minimum. This identifies the metal area Y1. The metal area identification data p1c after identification of the metal area Y1 becomes projection data extracting only the metal area Y1 from the actual measurement projection data p1.

[Step S14] Data Replacement

The data replacing unit 25, based on the metal area identification data p1c, carries out data replacement of the metal area Y1 of the actual measurement projection data p1 with data Z obtained from pixels K adjacent the metal area Y1, thereby to acquire replacement projection data p2 (see FIGS. 10(a) and 10(b)).

[Step S15] Generation of Replacement Reconstruction Image

The replacement image reconstruction unit 27 generates the replacement reconstruction image R2 by image reconstruction of the replacement projection data p2 (see FIG. 3(b)). The generated replacement reconstruction image R2 is an image without the metal area Y1.

[Step S16] Difference Process

The difference processing unit 29 determines a difference between the actual measurement projection data p1 and the replacement projection data p2, to acquire difference projection data p3 showing only the metal area Y1.

[Step S17] Generation of Difference Reconstruction Image

The difference image reconstruction unit 31 generates the difference reconstruction image R3 by image reconstruction of the difference projection data p3. The generated difference reconstruction image R3 is an image of only the metal area Y1 (see FIG. 3(c)).

[Step S18] Generation of Composite Reconstruction Image

The composite image generating unit 33 generates the composite reconstruction image R4 by selecting at least one image from among the actual measurement reconstruction image R1, replacement reconstruction image R2 and difference reconstruction image R3 on a pixel-by-pixel basis. The composite image generating unit 33 gives the pixel values (r2, r2+r3, r1) of images R1-R3 selected in step S02 and step S03 to the pixels r4 of the corresponding coordinates in the composite reconstruction image R4. The composite reconstruction image R4 is generated based on this. The generated composite reconstruction image R4 is displayed on the display unit 11, or is stored in the storage unit 13.

According to this embodiment, as described above, the actual measurement image reconstruction unit 21 carries out image reconstruction of the actual measurement projection data p1 to generate actual measurement reconstruction image R1. The metal area identifying unit 23 identifies the metal area Y1 of the actual measurement projection data p1 from the actual measurement projection data p1 and actual measurement reconstruction image R1 to acquire metal area identification data p1c. In the actual measurement projection data p1, for example, in a metal area such as of wire or screws, a resulting image has pixel values not so different from those of other areas, which makes it difficult to identify the metal area Y1 accurately. However, in the actual measurement reconstruction image R1, pixel values become remarkably large at boundaries between metal and body tissue, for example. By making use of this, boundaries between metal such as wire or screws and body tissue, for example, can be identified with increased accuracy. By using the actual measurement projection data p1 in addition to the actual measurement reconstruction image R1, it is possible to discriminate whether the inside of the boundary between metal and body tissue is the metal, for example. With these, a metal area can be identified with increased accuracy. The data replacing unit 25, based on the metal area identification data p1c, carries out data replacement of the metal area Y1 of the actual measurement projection data p1 with data Z obtained from pixels K adjacent the metal area Y1, thereby to acquire replacement projection data p2. The replacement image reconstruction unit 27 generates the replacement reconstruction image R2 without the metal area Y1 by image reconstruction of the replacement projection data p2. Since the metal area Y1 is identified with increased accuracy, the data replacement of the metal area Y1 can be carried out with increased accuracy. Therefore, the tissue adjacent the metal area Y1 of the tomographic image (replacement reconstruction image R2) can be restored with increased accuracy, while inhibiting artifacts due to the metal.

The difference processing unit 29 determines a difference between the actual measurement projection data p1 and the replacement projection data p2, to acquire difference projection data p3. The difference image reconstruction unit 31 carries out image reconstruction of the difference projection data p3 to generate the difference reconstruction image R3 of only the metal area Y1. And the composite image generating unit 33 generates the composite reconstruction image R4 by selecting at least one image from among the actual measurement reconstruction image R1, replacement reconstruction image R2 and difference reconstruction image R3 on a pixel-by-pixel basis. That is, the composite reconstruction image R4 is generated from not only the replacement reconstruction image R2 but the actual measurement reconstruction image R1 and difference reconstruction image R3. Since an optimal image is thereby selected for every pixel, a tomographic image (composite reconstruction image R4) showing metal in the metal area Y1 can be obtained while inhibiting artifacts due to the metal.

The metal area identifying unit 23, based on the graph cuts method, identifies the metal area Y1 of the actual measurement projection data p1 from the actual measurement projection data p1 and actual measurement reconstruction image R1, to acquire metal area identification data p1c. Consequently, the metal area Y1 can be identified with higher accuracy than by other methods.

The metal area identifying unit 23 determines seed areas in the graph cuts method based on threshold process results of the actual measurement projection data p1 and actual measurement reconstruction image R1. Consequently, based on the threshold process results, the seed areas in the graph cuts method can be set automatically. This facilitates identification of the metal area Y1.

At least one of the actual measurement image reconstruction unit 21, replacement image reconstruction unit 27 and difference image reconstruction unit 31 carries out image reconstruction based on an iterative approximation method. Consequently, image reconstruction can be carried out with high accuracy.

This invention is not limited to the foregoing embodiment, but may be modified as follows:

(1) In the foregoing embodiment, the metal area identifying unit 23, based on the graph cuts method, identifies the metal area Y1 of the actual measurement projection data p1 from the actual measurement projection data p1 and actual measurement reconstruction image R1 to acquire metal area identification data p1c, but this is not limitative. The metal area Y1 may be identified with area segmentation techniques such as a method using a static threshold, a method using a dynamic threshold, a method using snakes, a level set method and a grab cut method, for example. In these methods, although each is different in how to use the actual measurement reconstruction image R1, but they invariably create forward projection data.

Figure 13:
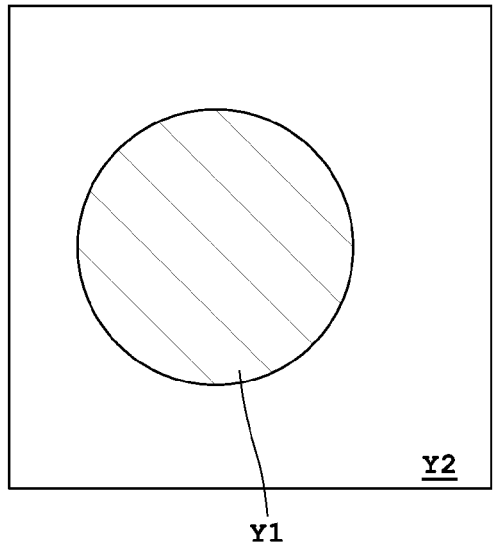
FIG. 13, (a) is a view showing actual measurement projection data after a threshold process according to a modification, (b) is a view showing forward projection data after the threshold process of the actual measurement reconstruction image according to the modification, and (c) is a view showing metal area identification data according to the modification.
Figure 13:
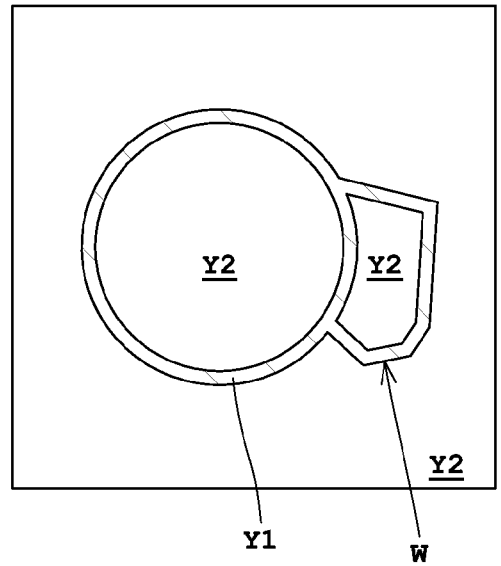
Figure 13:
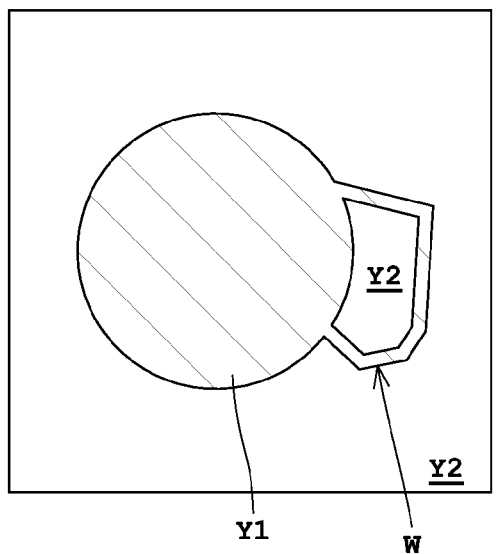
Figure 14:
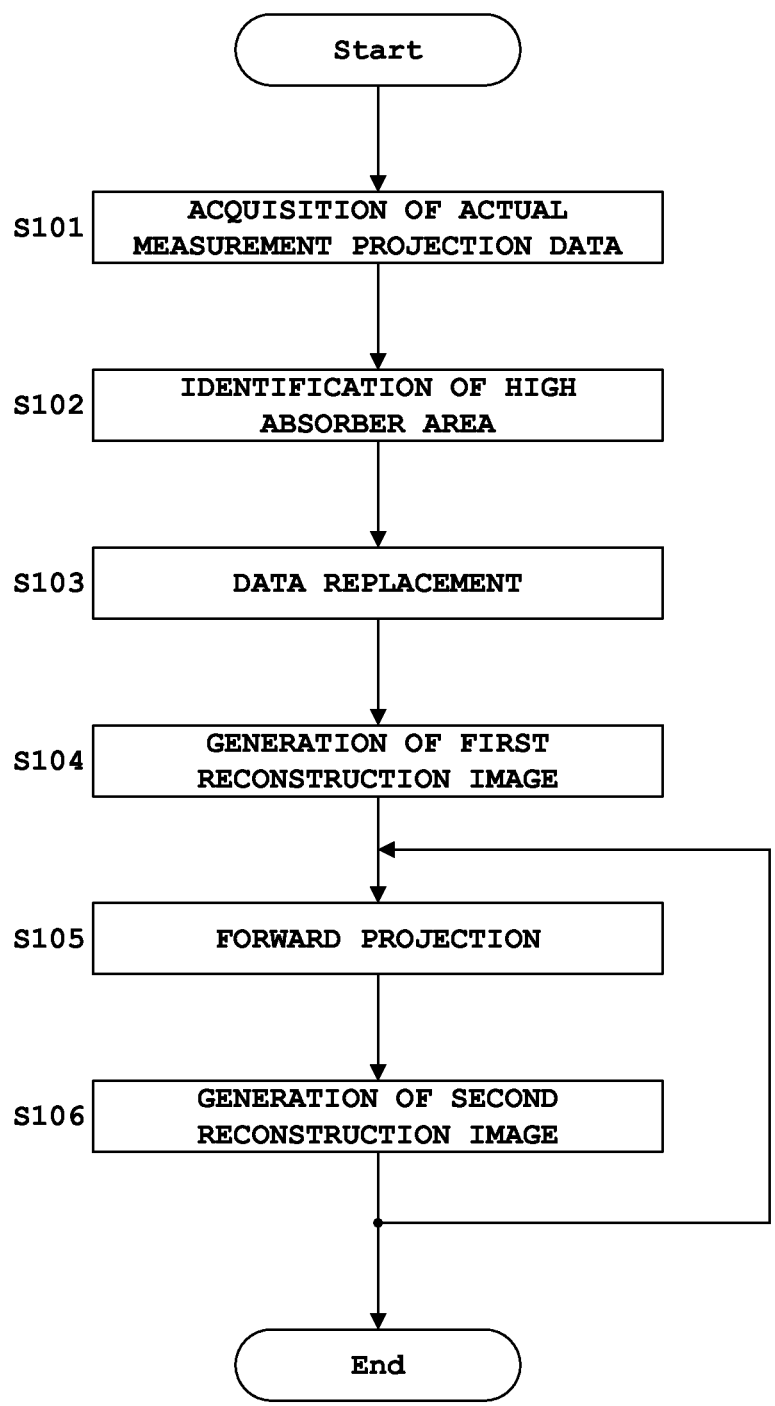
FIG. 14 is a flow chart showing operation of a conventional apparatus.

Here, the method using a static threshold will be described specifically as an example of the methods of identifying the metal area Y1. First, a static threshold process is carried out to extract the metal area Y1(="1") from the actual measurement projection data p1 (see FIG. 13(a)). The nonmetal area Y2 is indicated by "0". Next, the metal area Y1 on the actual measurement projection data p1 is extracted using the actual measurement reconstruction image R1 (see FIG. 13(b)). As in the embodiment, for example, a static threshold process is carried out on the actual measurement reconstruction image R1, and the actual measurement reconstruction image R1 after the threshold process is projected forward to create forward projection data. This extracts the metal area Y1 on the actual measurement projection data p1 shown in FIG. 13(b). The area discriminated as the metal area Y1 in at least one of FIGS. 13(a) and 13(b) is determined to be the metal area Y1 as end result (see FIG. 13(c)).

(2) In the foregoing embodiment and the modification (1), seeds are automatically set to the graph G used in the graph cuts method. However, for example, the actual measurement projection data p1 and actual measurement reconstruction image R1 are displayed on the display unit 11, and on the actual measurement projection data p1, the metal area Y1 and nonmetal area Y2 are designated from the input unit 12, and on the actual measurement reconstruction image R1, the metal area Y1 is designated from the input unit 12. And the metal area Y1 and nonmetal area Y2 designated on the actual measurement projection data p1 are set as seeds. The actual measurement reconstruction image R1 is projected forward with "1" set to the area designating the metal area Y1 and "0" set to the other area, and the pixel values of the forward projection data which are not "0" are set as seeds. That is, the metal area identifying unit 23, in response to the inputs from the input unit 12, sets seed areas in the graph cuts method from the actual measurement projection data p1 and actual measurement reconstruction image R1. As long as the seeds are set from the actual measurement projection data p1 and actual measurement reconstruction image R1, a graph cuts method different from the foregoing embodiment may be used.

(3) In the foregoing embodiment and each modification, the composite image generating unit 33 generates the composite reconstruction image R4 by selecting at least one image from among the actual measurement reconstruction image R1, replacement reconstruction image R2 and difference reconstruction image R3 on a pixel-by-pixel basis. However, instead of being limited to this, the composite reconstruction image R4 may be generated by selecting an image on a basis of every area of 2×2 pixels, for example.

Figure 11:
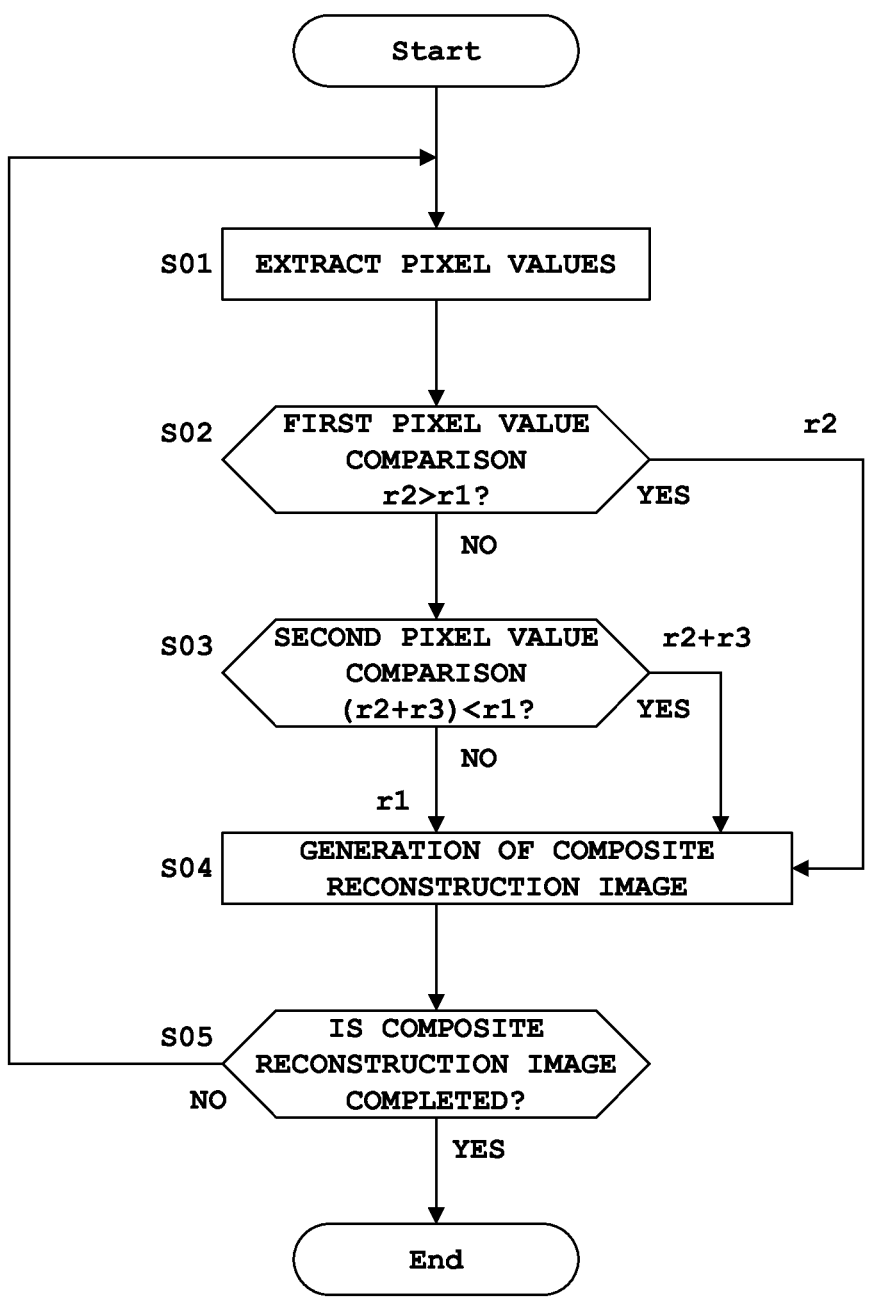
FIG. 11 is a flow chart illustrative of a composite image generating unit.

(4) In the foregoing embodiment and each modification, the composite image generating unit 33 may generate the composite reconstruction image R4 by omitting one of step S02 for correcting the undershooting pixel values and step S03 for correcting the overshooting pixel values such as of the metal area Y1 in the flow chart shown in FIG. 11. When step S02 is omitted and the determination in step S03 results in "No", pixel value r1 of the image R1 may be selected. Similarly, when step S03 is omitted and the determination in step S02 results in "No", pixel value r1 of the image R1 may be selected.

(5) In the foregoing embodiment and each modification, the X-ray tomographic image generator 20 may be in form of a personal computer, workstation or the like. That is, the X-ray tomographic image generator 20 may include a control unit in form of a CPU for executing programs, and a storage unit in form of storage media such as a ROM, RAM and so on for storing the programs and the like. The storage unit may store a program of operation in each of the steps S01-S05 and S11-S18, with the control unit executing such program. In this case, controls required for this program are inputted through the input unit 12, and the composite reconstruction image R4 after execution of the program is displayed on the display unit 11.

(6) In the foregoing embodiment and each modification, a program of operation in each of the steps S01-S05 and S11-S18 may be stored in the storage unit 13, which is executed by the main controller 9. In this case, controls required for this program are inputted through the input unit 12, and the composite reconstruction image R4 is displayed on the display unit 11, for example. Such operating program can be made executable on a personal computer connected to the X-ray tomographic apparatus 1 through a network system such as a LAN.

(7) In the foregoing embodiment and each modification, as shown in FIG. 1, the X-ray tomographic apparatus 1 acquires the acquired actual measurement projection data p1, with the X-ray tube 3 and FPD 4 moving parallel and in opposite directions to each other. However, the X-ray tomographic apparatus 1 may acquire the actual measurement projection data p1, with X-ray tube 3 and FPD 4 revolvable about the inspection object M.

(8) The foregoing embodiment and each modification have been described taking the X-ray tomographic apparatus 1 capable of tomosynthesis as an example of radiation tomographic apparatus. However, the radiation tomographic apparatus may be an X-ray CT apparatus.

(9) The foregoing embodiment and each modification have been described taking the FPD 4 as an example of actual measurement projection data acquiring unit, but it may be an image intensifier.

REFERENCE SIGNS LIST

1 . . . X-ray tomographic apparatus
4 . . . flat panel X-ray detector (FPD)
9 . . . main controller
20 . . . X-ray tomographic image generator
21 . . . actual measurement image reconstruction unit
23 . . . metal area identifying unit
25 . . . data replacing unit
27 . . . replacement image reconstruction unit
29 . . . difference processing unit
31 . . . difference image reconstruction unit
33 . . . composite image generating unit
th1, th2, th3 . . . thresholds
Y1 . . . metal area
Y2 . . . nonmetal area
Y3, Y3a . . . obscure areas
R4 . . . composite reconstruction image
G . . . graph
p1 . . . actual measurement projection data
p1a . . . projection data after threshold process
p1b . . . forward projection data
p1c . . . metal area identification data
p2 . . . replacement projection data
p3 . . . difference projection data
R1 . . . actual measurement reconstruction image
R2 . . . replacement reconstruction image
R3 . . . difference reconstruction image
R4 . . . composite reconstruction image
r1-r4 . . . pixel values
Z . . . replacement data

The invention claimed is:

1. A radiation tomographic image generating apparatus comprising:
    an actual measurement image reconstruction unit for carrying out image reconstruction of a plurality of actual measurement projection data acquired from different directions with respect to an inspection object including a high radiation absorber, to generate an actual measurement reconstruction image;
    a high absorber area identifying unit for identifying a high absorber area of the actual measurement projection data from the actual measurement projection data and the actual measurement reconstruction image, to acquire high absorber area identification data;
    a data replacing unit for carrying out, using the high absorber area identification data, data replacement of the high absorber area of the actual measurement projection data with data obtained from pixels adjacent the high absorber area, to acquire replacement projection data;
    a replacement image reconstruction unit for carrying out image reconstruction of the replacement projection data to generate a replacement reconstruction image;

a difference processing unit for determining a difference between the actual measurement projection data and the replacement projection data to acquire difference projection data;

a difference image reconstruction unit for carrying out image reconstruction of the difference projection data to generate a difference reconstruction image; and a composite image generating unit for generating a composite reconstruction image by selecting at least one image from among the actual measurement reconstruction image, the replacement reconstruction image and the difference reconstruction image on an area-by-area basis.

2. The radiation tomographic image generating apparatus according to claim 1, wherein, of pixel values of the same coordinates in the actual measurement reconstruction image and the replacement reconstruction image, when the pixel value in the replacement reconstruction image is larger than the pixel value in the actual measurement reconstruction image, the composite image generating unit generates the composite reconstruction image by selecting the pixel value of the replacement reconstruction image.

3. The radiation tomographic image generating apparatus according to claim 1, wherein, of pixel values of the same coordinates in the actual measurement reconstruction image, the replacement reconstruction image and the difference reconstruction image, when a sum of the pixel value in the replacement reconstruction image and the pixel value in the difference reconstruction image is smaller than the pixel value in the actual measurement reconstruction image, the composite image generating unit generates the composite reconstruction image by selecting a pixel value of the sum.

4. The radiation tomographic image generating apparatus according to claim 1, wherein, of pixel values of the same coordinates in the actual measurement reconstruction image, the replacement reconstruction image and the difference reconstruction image, when a sum of the pixel value in the replacement reconstruction image and the pixel value in the actual measurement reconstruction image is larger than the pixel value in the difference reconstruction image, the composite image generating unit generates the composite reconstruction image by selecting the pixel value in the actual measurement reconstruction image.

5. The radiation tomographic image generating apparatus according to claim 1, wherein the high absorber area identifying unit, based on a graph cuts method, identifies the high absorber area of the actual measurement projection data from the actual measurement projection data and the actual measurement reconstruction image, to acquire the high absorber area identification data.

6. The radiation tomographic image generating apparatus according to claim 5, wherein the high absorber area identifying unit sets seed areas in the graph cuts method based on threshold process results of the actual measurement projection data and the actual measurement reconstruction image.

7. The radiation tomographic image generating apparatus according to claim 1, wherein at least one of the actual measurement image reconstruction unit, the replacement image reconstruction unit and the difference image reconstruction unit carries out image reconstruction based on an iterative approximation method.

8. A radiation tomographic image generating method comprising:

a step of carrying out image reconstruction of a plurality of actual measurement projection data acquired from different directions with respect to an inspection object including a high radiation absorber, to generate an actual measurement reconstruction image;

a step of identifying a high absorber area of the actual measurement projection data from the actual measurement projection data and the actual measurement reconstruction image, to acquire high absorber area identification data;

a step of carrying out, using the high absorber area identification data, data replacement of the high absorber area of the actual measurement projection data with data obtained from pixels adjacent the high absorber area, to acquire replacement projection data;

a step of carrying out image reconstruction of the replacement projection data to generate a replacement reconstruction image: and a step of generating a composite reconstruction image by selecting one image from the actual measurement reconstruction image and the replacement reconstruction image on an area-by-area basis.

* * * * *